United States Patent
Jonniaux et al.

(10) Patent No.: US 6,518,047 B1
(45) Date of Patent: Feb. 11, 2003

(54) ENZYME OR CELL PREPARATION WITH INULINASE ACTIVITY

(75) Inventors: Jean-Luc Jonniaux, Tienen (BE); Karl Rauw, Kettenis (BE); Philippe Thonart, La Bruyere (BE); Thierry Dauvrin, Couthuin (BE)

(73) Assignee: Puratos Naamloze Vennootschap, Groot-Bijgaarden (BE)

( * ) Notice: Subject to any disclaimer, the term of this patent is extended or adjusted under 35 U.S.C. 154(b) by 0 days.

(21) Appl. No.: 10/006,937

(22) Filed: Nov. 9, 2001

(30) Foreign Application Priority Data

Nov. 9, 2000 (EP) .............................. 00870264

(51) Int. Cl.[7] .............................. C12P 19/04
(52) U.S. Cl. .............................. 435/101
(58) Field of Search .............................. 435/200

(56) References Cited

FOREIGN PATENT DOCUMENTS

| EP | 0043169 | 10/1983 |
|---|---|---|
| WO | WO 9413821 A | 6/1994 |

OTHER PUBLICATIONS

Arand, M and Golubev AM et al, 2001 Exo–insulinase from *Aspergillus awamori* var. 2250: enzymatic properties, sequence analysis and preliminary X–ray data. EMBL Acc# AJ315793.*

European Search Report from EP00870264 dated Apr. 26, 2001.

Onodera, et al., (1996) *Molecular Cloning and Nucleotide Sequences of cDNA and Gene Encoding endo–Inulinase from Penicillium Purpurogenum.* Biosci. Biotech.Biochem. 60(11)1780–1785.

Rehm, et al. (1998) *Production of 1–Kestose in Transgenic Yeast Expressing a Fructosyltransferase from Aspergillus foetidus.* J.Bacteriology. 180(5)1305–1310.

Onodera; EMBL/GENBANK/DDBJ databases; *Penicillium Purpurogenum DNA for endo–inulinase Precursor, complete cds*; 2 pgs.; Feb. 1/97 (created), Jan. 21/99 (Last updated).

Chapman, et al.; EMBL/GENBANK/DDBJ databases; *Kluyveromyces Marxianus, Inulinase Preprotein*; 2 pg.; Mar. 3/98 (Created), Mar. 11/98 (Last Updated).

Rehm; EMBL/GENBANK/DDBJ databases; *Aspergillus Foetidus DNA for Sucrose: Sucrose 1–Fructosyltransferase Gene*; 2 pgs; Mar. 3/98 (Created), Mar. 11/98 (Last updated).

Vandamme, et al. (1983) *Microbial Inulinases: Fermentation Process, Properties, and Applications*; Advances in Applied Microbiology, 29:139–177.

Boel, et al. (1984) *Two Different Types of Intervening Sequences in the Glucoamylase Gene from Aspergillus niger*, EMBO Journal 3(7):1581–1585.

Punt, et al. (1990) *Functional Elements in the Promoter Region of the Aspergillus nidulans gpdA Gene Encoding Glyceraldehyde–3–phosphate dehydrogenase*, Gene, 93:101–109.

Ettalibi, et al. (1990) *Molecular and Kinetic Properties of Aspergillus ficuum Inulinases*, Agric.Biol.Chem. 54(1)61–68.

(List continued on next page.)

Primary Examiner—Ponnathapu Achutamurthy
Assistant Examiner—Sheridan L. Swope
(74) Attorney, Agent, or Firm—Knobbe, Martens, Olson & Bear, LLP

(57) ABSTRACT

The present invention is related to an isolated and purified enzyme with inulinolytic activity having more than 75% sequence identity with the amino acid sequence SEQ ID NO 12 to its encoding nucleotidic sequence to a cell producing the enzyme and to the use for the degradation of inulin or inulin-containing plant material, especially for the production of fructose syrups and for the production of oligomers of fructose.

4 Claims, 10 Drawing Sheets

OTHER PUBLICATIONS

Hynes, et al. (1983) *Isolation of Genomic Clones Containing amdS Gene of Aspergillus nidulans and Their Use in the Analysis of Structural and Regulatory Mutations*, Molecular and Cellular Biology, 3(8)1430–1439.

Punt, et al. (1991) *Intracellular and Extracellular Production of Proteins in Aspergillus Under the Control of Expression Signals of the Highly Expressed Aspergillus nidulans gpdA Gene*, J.Biotech. 17:19–34.

Pessoni, et al. (1999) *Extracellular Inulinases from Penicillium janczewskii, a Fungus Isolated From the Rhizosphere of Vernonia herbacea(Asteraceae)*, J.Applied Micro. 87:141–147.

Miller, G.L. (1959) *Use of Dinitrosalicylic Acid Reagent for Determination of Reducing Sugar*, Anal. Chem. 31(3)426–428.

Pandey, et al. (1999) *Recent Developments in Microbial Inulinases*, Applied Biochemistry and Biotechnology 81:35–52.

* cited by examiner

```
               9              18              27              36              45              54
5'  GCA GAT TCG ATC TGG TTA GGC CAT ATC GAA CTT CAG TCC GTC AAC AGC ACA GTG 63              72              81              90              99             108
    GGA CCG CCA TTG TAC GGC ACC ATA CGG CAG GAC GAA GTA TGC CAA TGC ACA AAC 117             126             135             144             153             162
    ATC GTG GAT AGG TCG GGG ATA CTT TGC AGC AGC ATG GCG CCG AGT GAT TAG GGA 171             180             189             198             207             216
    GGT GGT TAC ATC AAA CGC AAA AGA GGA TCA TGG CGA TAC AAA GAC ATT GGT GAA 225             234             243             252             261             270
    GCC GGC GGT GGA GAC TGA AAA GGG AAA GCA GGG GAA ACT CGC GTG GCT GGC AGG 279             288             297             306             315             324
    GGT ATA AGC CGA GTA TAC GCC GTG ATG TCC GAA ATT ATC GCT GGG TTT GAG CGA 333             342             351             360             369             378
    TCT CGG TGC CGA AGC GTG CAG AAT CTA GTG CTC AGC AGG AAA CAT TGT GGA TCT 387             396             405             414             523             432
    AAG TTT ATA ATT CTC GGA AGA AAC ATC GGC GCG GAT GAC GAT CGT CCA GCA GGT 441             450             459             468             477             486
    GGT GAC ATA CCC CGT GGG GAA TGG AGA CAT TGG GAA AAG ATA TAA ATA CTG CTT 495             504             513             522             531             540
    GGA ATA ATT GTG AAG GAA TAT TTT CAT TCA AGC GCT TCA CTT TCT TTT ATT CCT 549             558             567             576             585             594
    TTT TTT TTC TTG CTC CTT GCA TAA CTC CAC GAT GCT CAA GTT TGC GAG CGC CTT
                                                     M   L   K   F   A   S   A   F 603             612             621             630             639             648
    CGT GTT GGG TCT CCT GGC GGG ACC CAC TGT GGC CGT GAA CTA TAC GGA ACC CTT
     V   L   G   L   L   A   G   P   T   V   A   V   N   Y   T   E   F   F 657             666             675             684             693             702
    TCG GCC TCA GTA TCA CTT CTC TCC TGC TAA GCA CTG GAC GAA TGA TCC CGC TGG
     R   P   Q   Y   H   F   S   P   A   K   W   T   T   N   D   P   A   G
```

FIG. 5B

```
      711          720          729          738          747          756
TCT CTT CTA TTA CGA TGG CAC CTA CCA TAT GTT CTT CCA GTA CAA CCC CGG TGG
 L   F   Y   Y   D   G   T   Y   M   M   F   F   Q   Y   N   P   G   G 765          774          783          792          801          810
TAT TGA ATG GGG CAA CAT GTC CTG GGG TCA TGC TAC CAG CAA AGA TCT GAC CCA
 I   E   N   G   Q   H   V   L   G   S   C   Y   Q   Q   R   S   D   P 819          828          837          846          855          864
CTG GGA CGA GCA GCC TGT TGC GCT TCT CGC AAA GGG TTA CCC CAA CAA CGT CAC
 W   D   E   Q   F   V   A   L   L   A   K   G   Y   F   N   N   V   T 873          882          891          900          909          918
TGA GAT GTA TTT CAC TGG AAG TGC CGT GGC CGA TGT CAA CAA CAC CAG CGG TTT
 E   M   Y   F   T   G   S   A   V   A   D   V   N   N   T   S   G   F 927          936          945          954          963          972
CGG CAC AGA TGG CAA GGT TCC CTT GGT CGC TAT CTA CAC CTC TTA CGT GAG TAT
 G   T   D   G   K   V   P   L   V   A   I   Y   T   B   Y 981          990          999         1008         1017         1026
TCG ACC TAG TTT CTT TTC TTG CGT AGC ACT AAA TTG ACC ATC ATT CTT CCT TCA 1035         1044         1053         1062         1071         1080
TAG TAT ACC GTC ACA CAA ACC CTG CCC AGC GGC AAG CGA GTT CAC AAA GAC CAG
     Y   T   V   T   Q   T   L   P   S   G   K   K   V   H   K   D   Q 1089         1098         1107         1116         1125         1134
CAG TCT CAG TCA ATT GCC TAC AGT CTG GAC AAT GGC ATG ACA TGG ACA CCG TAC
 Q   S   Q   S   I   A   Y   S   L   D   N   G   M   T   W   T   P   Y 1143         1152         1161         1170         1179         1185
GAC TCT GTC AAC CCT GTG ATC CAC TAC CCT CCC CCG CCC TAC CAC AGC CAG TAC
 D   S   V   N   P   V   I   H   Y   P   P   P   P   Y   H   S   Q   Y 1197         1206         1215         1224         1233         1242
AAG AAC TTC CGT GAC CCG TTC GTG TTC TGG CAC GAC CAG ACC CAG CGA TGG ATT
 K   N   F   R   D   P   F   V   F   W   H   D   Q   T   Q   R   W   I 1251         1260         1269         1278         1287         1296
CTC GTC ACC ACC CTG GCT GAA CTG CAC AAG CTC GTG ATC TGG ACA TCC GAC AAT
 L   V   T   T   L   A   E   L   H   K   L   V   I   W   T   S   D   N 1305         1314         1323         1332         1341         1350
CTC AAG GAC TGG ACC GTC CTC AGC GAA TTC GGC CCC TAC AAT GGC GTC GGG GGT
 L   K   D   W   T   V   L   S   E   F   G   P   Y   N   D   V   G   G
```

FIG.5C

```
      1359        1368        1377        1386        1395        1404
GTG TGG GAG TGC CCC AAC CTC TTC CCT CTT CCA GTT GAC GGT GAC GGT GAC GAG
 V   W   E   C   P   N   L   F   P   L   P   V   D   G   D   G   D   N 1413        1422        1431        1440        1449        1458
AAC ATG ACC AAG TGG GTC ATG GTC GTT GGA CTC AAC CCC GGC GGA CCA CCT GGT
 N   M   T   K   W   V   M   V   V   G   L   N   P   G   G   P   P   G 1467        1476        1485        1494        1503        1512
ACT GTC GGT TCC GGA ACA CAG TAC TTT ATC GGC AAC TTC AAT GGC ACA GCC TTT
 T   V   G   S   G   T   Q   Y   F   I   G   N   F   N   G   T   A   F 1521        1530        1539        1548        1557        1566
ATT CCG GAT GCC GAT ACC ATC TAC CCC GGA AAC AAG ACT GCC AAC TGG ATG GAC
 I   P   D   A   D   T   I   Y   P   G   N   K   T   A   N   W   M   D 1575        1584        1593        1602        1611        1620
TGG GGC CCG GAC TTC TAC GCT GCT GCC GCT TAC AAC GGT CTC CCT AAG GAG GAC
 W   G   P   D   F   Y   A   A   A   A   Y   N   G   L   P   K   E   D 1629        1638        1647        1656        1665        1674
CAT GTC CAG CTC GCA TGG ATG AAT AAC TGG CAA TAT GGT GAA CAT ATC CCG ACT
 H   V   Q   L   A   W   M   N   N   W   Q   Y   G   E   H   I   P   T 1683        1692        1701        1710        1719        1728
CAC CCC TGG CGA AGC GCG ATG GCT ATC CCT CGT CAC CTG TCT CTG AAG AAC ATC
 H   P   W   R   S   A   M   A   I   P   R   H   L   S   L   K   N   I 1737        1746        1755        1764        1773        1782
CAC CCC TGG CGA AGC GCG ATG GCT ATC CCT CGT CAC CTG TCT CTG AAG AAC ATC
 D   S   K   T   T   L   V   Q   Q   P   H   V   N   W   K   S   I   K 1791        1800        1809        1818        1827        1836
GGC AAG CAT GCT TAC ACC CGC TTC TGG AAG AGT GTC GAC GAA GGC ATC ACA GAC
 G   K   H   A   Y   T   R   F   W   K   S   V   D   E   G   I   T   D 1845        1854        1863        1872        1881        1890
CTC GGA CCT CTG GGC AAG ACA CTT GCA ATC GAT ATA ACC TTT TCC ACG CCC AAG
 L   G   P   L   G   K   T   L   A   I   D   I   T   F   S   T   P   K 1899        1908        1917        1926        1935        1944
GAC GCT GGT TCT CAG ACC TTT CAG TTC GGA ATC GTC GTC CAG GCC ACG GAA GAC
 D   A   G   S   Q   T   F   Q   F   G   I   V   V   Q   A   T   E   D
```

FIG. 5D

```
         1953        1962        1971        1980        1989        1998
    TTG TCC CAA CAC ACG CGA GTC GGG TAT GAT TTC CAG AGT CAG CAG GTC TTC TTG
     L   S   Q   H   T   K   V   G   Y   D   F   Q   S   Q   Q   V   F   L 2007        2016        2025        2034        2043        2052
    GAC CGC ACG CAT TCG GGA ATT GTC TCA TTC GAC AAG ACC TTC CCG ACC GTG TAT
     D   R   T   M   S   G   I   V   S   F   D   K   T   F   P   T   V   Y 2061        2070        2079        2088        2097        2106
    AAC ACC ACT CTT GCA CCG TGC TCA GAT GGA GAA GTC CGT TTG CAG CTC TTG GTG
     N   T   T   L   A   P   C   S   D   G   E   V   R   L   Q   L   L   V 2115        2124        2133        2142        2151        2160
    GAC TGG TCT AGC GTT GAG GTC TTT GGT GGT GAG GGC GAG AAG ACC GTG ACA GCC
     D   W   S   S   V   E   V   F   G   G   E   G   E   K   T   V   T   A 2169        2178        2187        2196        2205        2214
    CAG ATC TTT CCG AAC GAG GAG GCC ACA CAT GTT GAG CTC TTC TCG ACT GGT GGA
     Q   I   F   P   N   E   E   A   T   H   V   E   L   F   S   T   G   G 2223        2232        2241        2250        2259        2268
    AGC ACT GGG AAT GTC AAG GTT GAA ATC TGG GAT GTG TCC TCG ATT TGG AAC TGA
     S   T   G   N   V   K   V   E   I   W   D   V   S   S   I   W   N   *

2277        2286        2295        2304        2313        2322
    CTG GTG CAC CGT TAG AAA ATA AGA GTA TAG AAT AGT CCA GGT AGC AAA ATA AAG 2331        2340        2349        2358        2367        2376
    CTA TTG GCG ACA TGT CCA TTC AAG ATT GGG ACC TTC CAA ACG GTG CAT CGA ATC 2385        2394        2403        2412        2421        2430
    ATA AAG TCT CTT GAA ATC ACA CAT ATA CAT ACG TAC ATA CAA ACA GCT CAA ACT 2439        2448        2457        2466        2475        2484
    CAA TCA CAA ACA ACA AGC GTT CCT CAG AAG CAT TGT CCG TTC GAA TGT CTC CAT 2493        2502        2511        2520        2529        2538
    CAA ATC AAT GAC CCT CGC AGT TAC CTC CTT GCA CTC CTC ATT GAC ATC GCC TCC 2547        2556        2565        2574        2583        2592
    ATC GAT AAT ATC CCC GAA TCG ACG CTT CCA GAA CCG CCA TCT ATC AAG GGA AAG 2601        2610        2619        2628        2637        2646
    ACT GGC CTT GCC ATG ATA TAG GGG ATC AGG TTC CCA ACC CTT CCA TTC ATT GGA
```

```
          2655      2664      2673      2682      2691      2700
CGA CCC CTG GTA AAG ATC CGG CTA TGA CGT AAG TTC GAA CAA GCT CTG ACC ATA
          2709      2718      2727      2736      2745     -2754
CCA CAG AAT CCA TTG GGC CGC GCG CGC CTA GGA CGA AAG CAC TTC GCA CTT CTT
          2763      2772      2781      2790      2799      2808
TAT CTT TAC AGG ACA GAT CAT TCT CCA AAG CGA AAC GCA TAG CCC AGA TTA CAT
          2817      2826      2835      2844      2853      2862
ATG TCG GGT CGC ATC CGG AAA CAC GCT GCT CAT GGA GGT GGC CAC AAA TGA GTT
          2870
ATA GTT CA 3'
```

FIG. 5E

SEQUENCE LISTING

<160> NUMBER OF SEQ ID NOS: 15

<210> SEQ ID NO 1

-continued

```
<211> LENGTH: 21
<212> TYPE: PRT
<213> ORGANISM: Penicillium restrictum A191
<220> FEATURE:
<221> NAME/KEY: VARIANT
<222> LOCATION: (1)...(21)
<223> OTHER INFORMATION: Xaa = Any Amino Acid

<400> SEQUENCE: 1

Leu Xaa Tyr Thr Glu Pro Tyr Arg Xaa Gln Tyr Thr Phe Xaa Pro Asp
 1               5                  10                  15

Gln Glu Asn Xaa Xaa
            20

<210> SEQ ID NO 2
<211> LENGTH: 11
<212> TYPE: PRT
<213> ORGANISM: Penicillium restrictum A191

<400> SEQUENCE: 2

Asp Leu Thr His Trp Asp Glu Gln Pro Val Ala
 1               5                  10

<210> SEQ ID NO 3
<211> LENGTH: 15
<212> TYPE: DNA
<213> ORGANISM: Artificial Sequence
<220> FEATURE:
<223> OTHER INFORMATION: primer for N-terminal sequence of P. restrictum
      A191
<221> NAME/KEY: modified_base
<222> LOCATION: 12
<223> OTHER INFORMATION: I
<221> NAME/KEY: misc_feature
<222> LOCATION: (1)...(15)
<223> OTHER INFORMATION: n = A,T,C or G

<400> SEQUENCE: 3
ccacartaya cnttc                                                    15

<210> SEQ ID NO 4
<211> LENGTH: 20
<212> TYPE: DNA
<213> ORGANISM: Artificial Sequence
<220> FEATURE:
<223> OTHER INFORMATION: primer for internal fragment of P. restrictum
      A191
<221> NAME/KEY: misc_feature
<222> LOCATION: (1)...(20)
<223> OTHER INFORMATION: n = A,T,C or G

<400> SEQUENCE: 4
acnggytgyt crtcccaatg                                               20

<210> SEQ ID NO 5
<211> LENGTH: 174
<212> TYPE: DNA
<213> ORGANISM: Penicillium restrictum A191
<220> FEATURE:
<221> NAME/KEY: misc_feature
<222> LOCATION: (1)...(174)
<223> OTHER INFORMATION: n = A,T,C or G

<400> SEQUENCE: 5
cacagtatca cttntctcct gctaagcact ggacgaatga tcccgctggt ctcttctatt     60
acgatggcac ctaccatatg ttcttccagt acaaccccgg tggtattgaa tggggcaaca    120
tgtcctgggg tcatgctacc agcaaagatc tgacccattg ggacgagcaa ccct          174
```

-continued

<210> SEQ ID NO 6
<211> LENGTH: 57
<212> TYPE: PRT
<213> ORGANISM: Penicillium restrictum A191
<220> FEATURE:
<221> NAME/KEY: VARIANT
<222> LOCATION: (1)...(57)
<223> OTHER INFORMATION: Xaa = Any Amino Acid

<400> SEQUENCE: 6

Gln Tyr His Xaa Ser Pro Ala Lys His Trp Thr Asn Asp Pro Ala Gly
 1               5                  10                  15

Leu Phe Tyr Tyr Asp Gly Thr Tyr His Met Phe Phe Gln Tyr Asn Pro
            20                  25                  30

Gly Gly Ile Glu Trp Gly Asn Met Ser Trp Gly His Ala Thr Ser Lys
        35                  40                  45

Asp Leu Thr His Trp Asp Glu Gln Pro
    50                  55

<210> SEQ ID NO 7
<211> LENGTH: 18
<212> TYPE: DNA
<213> ORGANISM: Artificial Sequence
<220> FEATURE:
<223> OTHER INFORMATION: primer for sequencing

<400> SEQUENCE: 7
tctcctgcta agcactgg                                                       18

<210> SEQ ID NO 8
<211> LENGTH: 23
<212> TYPE: DNA
<213> ORGANISM: Artificial Sequence
<220> FEATURE:
<223> OTHER INFORMATION: primer for sequencing

<400> SEQUENCE: 8
atgggtcaga tctttgctgg tag                                                 23

<210> SEQ ID NO 9
<211> LENGTH: 2867
<212> TYPE: DNA
<213> ORGANISM: Artificial Sequence
<220> FEATURE:
<223> OTHER INFORMATION: partial nucleotide sequence from pPRINU
      plasmid insert comprising inulinase coding sequence

<400> SEQUENCE: 9
cagattcgat ctggttaggc catatcgaac ttcagtccgt cacgcacagt gggaccgcca         60
ttgtacggca ccatcggca ggacgaagta tgccaatgca caaacatcgt ggataggtcg         120
gggatacttt gcagcagcat ggcgccgagt gattagggag gtggttacat caaacgcaaa        180
agaggatcat ggcgatacaa agacattggt gaagccggcg gtgagactg aaagggaaa          240 gcagggaaa ctcgcgtggc tggcagggt ataagccgag tatacgccgt gatgtccgaa          300
attatcgctg ggtttgagcg atctcggtgc cgaagcgtgc agaatctagt gctcagcagg        360
aaacattgtg gatctaagtt tataattctc cgaagaaaca tcggcgcgga tgacgatcgt        420
ccagcaggtg gtgacatacc ccgtggggaa tggagacatt gggaaaagat ataaatactg        480
cttggaataa ttgtgaagga atattttcat tcaagcgctt cactttcttt tattccttt         540 ttttcttgc tccttgcata actccacgat gctcaagttt gcgagcgcct tcgtgttggg         600

-continued

```
tctcctggcg ggacccactg tggccgtgaa ctatacggaa ccctttcggc ctcagtatca      660
cttctctcct gctaagcact ggacgaatga tcccgctggt ctcttctatt acgatggcac      720
ctaccatatg ttcttccagt acaaccccgg tggtattgaa tggggcaaca tgtcctgggg      780
tcatgctacc agcaaagatc tgacccactg gacgagcag cctgttgcgc ttctcgcaaa       840
gggttacccc aacaacgtca ctgagatgta tttcactgga agtgccgtgg ccgatgtcaa      900
caacaccagc ggtttcggca cagatggcaa ggttcccttg gtcgctatct acacctctta      960
cgtgagtatt cgacctagtt tcttttcttg cgtagcacta aattgaccat cattcttcct     1020
tcatagtata ccgtcacaca aaccctgccc agcggcaagc gagttcacaa agaccagcag     1080
tctcagtcaa ttgcctacag tctggacaat ggcatgacat ggacaccgta cgactctgtc     1140
aaccctgtga tccactaccc tcccccgccc taccacagcc agtacaagaa cttccgtgac     1200
ccgttcgtgt tctggcacga ccagacccag cgatggattc tcgtcaccac cctggctgaa     1260
ctgcacaagc tcgtgatctg acatccgac aatctcaagg actggaccgt cctcagcgaa      1320
ttcggcccct acaatggcgt cggggtgtgt gggagtgcc ccaacctctt ccctcttcca      1380
gttgacggtg acggtgacga gaacatgacc aagtgggtca tggtcgttgg actcaaccc     1440 ggcggaccac ctggtactgt cggttccgga acacagtact ttatcggcaa cttcaatggc     1500
acagccttta ttccggatgc cgataccatc taccccggaa acaagactgc caactggatg     1560
gactggggcc cggacttcta cgctgctgcc gcttacaacg gtctccctaa ggaggaccat     1620
gtccagctcg catggatgaa taactggcaa tatggtgaac atatcccgac tcacccctgg     1680
cgaagcgcga tggctatccc tcgtcacctg tctctgaaga catcgactc gaagacgact      1740 ctcgtccagc agccacacgt gaactggaaa tcgatcaagg gcaagcatgc ttacacccgc     1800
ttctggaaga gtgtcgacga aggcatcaca gacctcggac ctctgggcaa gacacttgca     1860
atcgatataa cctttttccac gcccaaggac gctggttctc agaccttttca gttcggaatc    1920 gtcgtccagg ccacggaaga cttgtcccaa cacacgcgag tcgggtatga tttccagagt     1980
cagcaggtct tcttggaccg cacgcattcg ggaattgtct cattcgacaa gaccttcccg     2040
accgtgtata acaccactct tgcaccgtgc tcagatggag aagtccgttt gcagctcttg     2100
gtggactggt ctagcgttga ggtctttggt ggtgagggcg agaagaccgt gacagcccag     2160
atctttccga acgaggaggc cacacatgtt gagctcttct cgactggtgg aagcactggg     2220
aatgtcaagg ttgaaatctg ggatgtgtcc tcgatttgga actgactggt gcaccgttag     2280
aaaataagag tatagaatag tccaggtagc aaaataaagc tattggcgac atgtccattc     2340
aagattggga ccttccaaac ggtgcatcga atcataaagt ctcttgaaat cacacatata     2400
catacgtaca tacaaacagc tcaaactcaa tcacaaacaa caagcgttcc tcagaagcat     2460
tgtccgttcg aatgtctcca tcaaatcaat gaccctcgca gttacctcct tgcactcctc     2520
attgacatcg ccttcatcga taatatcccc gaatcgacgc ttccagaacc gccatctatc     2580
aagggaaaga ctggccttgc catgatatag gggatcaggt tcccaaccct tccattcatt     2640
ggacgacccc tggtaaagat ccggctatga cgtaagttcg aacaagctct gaccatacca     2700
cagaatccat tgggccgcgc gcgcctagga cgaaagcact tcgcacttct ttatcttttac    2760 aggacagatc attctccaaa gcgaaacgca tagcccagat tacatatgtc gggtcgcatc     2820
cggaaacacg ctgctcatgg aggtggccac aaatgagtta tagttca                   2867
```

<210> SEQ ID NO 10

```
<211> LENGTH: 131
<212> TYPE: PRT
<213> ORGANISM: Artificial Sequence
<220> FEATURE:
<223> OTHER INFORMATION: coding region from partial nucleotide sequence
      from  pPRINU plasmid insert

<400> SEQUENCE: 10

Met Leu Lys Phe Ala Ser Ala Phe Val Leu Gly Leu Ala Gly Pro
 1               5                  10                  15

Thr Val Ala Val Asn Tyr Thr Glu Pro Phe Arg Pro Gln Tyr His Phe
                20                  25                  30

Ser Pro Ala Lys His Trp Thr Asn Asp Pro Ala Gly Leu Phe Tyr Tyr
            35                  40                  45

Asp Gly Thr Tyr His Met Phe Phe Gln Tyr Asn Pro Gly Gly Ile Glu
        50                  55                  60

Trp Gly Asn Met Ser Trp Gly His Ala Thr Ser Lys Asp Leu Thr His
 65                  70                  75                  80

Trp Asp Glu Gln Pro Val Ala Leu Leu Ala Lys Gly Tyr Pro Asn Asn
                85                  90                  95

Val Thr Glu Met Tyr Phe Thr Gly Ser Ala Val Ala Asp Val Asn Asn
                100                 105                 110

Thr Ser Gly Phe Gly Thr Asp Gly Lys Val Pro Leu Val Ala Ile Tyr
            115                 120                 125

Thr Ser Tyr
    130

<210> SEQ ID NO 11
<211> LENGTH: 412
<212> TYPE: PRT
<213> ORGANISM: Artificial Sequence
<220> FEATURE:
<223> OTHER INFORMATION: coding region from partial nucleotide sequence
      from  pPRINU plasmid insert

<400> SEQUENCE: 11

Tyr Thr Val Thr Gln Thr Leu Pro Ser Gly Lys Arg Val His Lys Asp
 1               5                  10                  15

Gln Gln Ser Gln Ser Ile Ala Tyr Ser Leu Asp Asn Gly Met Thr Trp
                20                  25                  30

Thr Pro Tyr Asp Ser Val Asn Pro Val Ile His Tyr Pro Pro Pro
            35                  40                  45

Tyr His Ser Gln Tyr Lys Asn Phe Arg Asp Pro Phe Val Phe Trp His
    50                  55                  60

Asp Gln Thr Gln Arg Trp Ile Leu Val Thr Thr Leu Ala Glu Leu His
 65                  70                  75                  80

Lys Leu Val Ile Trp Thr Ser Asp Asn Leu Lys Asp Trp Thr Val Leu
                85                  90                  95

Ser Glu Phe Gly Pro Tyr Asn Gly Val Gly Val Trp Glu Cys Pro
                100                 105                 110

Asn Leu Phe Pro Leu Pro Val Asp Gly Asp Gly Asp Glu Asn Met Thr
            115                 120                 125

Lys Trp Val Met Val Val Gly Leu Asn Pro Gly Pro Pro Gly Thr
                130                 135                 140

Val Gly Ser Gly Thr Gln Tyr Phe Ile Gly Asn Phe Asn Gly Thr Ala
145                 150                 155                 160

Phe Ile Pro Asp Ala Asp Thr Ile Tyr Pro Gly Asn Lys Thr Ala Asn
                165                 170                 175
```

-continued

```
Trp Met Asp Trp Gly Pro Asp Phe Tyr Ala Ala Ala Tyr Asn Gly
            180                 185                 190

Leu Pro Lys Glu Asp His Val Gln Leu Ala Trp Met Asn Asn Trp Gln
            195                 200                 205

Tyr Gly Glu His Ile Pro Thr His Pro Trp Arg Ser Ala Met Ala Ile
            210                 215                 220

Pro Arg His Leu Ser Leu Lys Asn Ile Asp Ser Lys Thr Thr Leu Val
225                 230                 235                 240

Gln Gln Pro His Val Asn Trp Lys Ser Ile Lys Gly Lys His Ala Tyr
                245                 250                 255

Thr Arg Phe Trp Lys Ser Val Asp Glu Gly Ile Thr Asp Leu Gly Pro
            260                 265                 270

Leu Gly Lys Thr Leu Ala Ile Asp Ile Thr Phe Ser Thr Pro Lys Asp
            275                 280                 285

Ala Gly Ser Gln Thr Phe Gln Phe Gly Ile Val Val Gln Ala Thr Glu
            290                 295                 300

Asp Leu Ser Gln His Thr Arg Val Gly Tyr Asp Phe Gln Ser Gln Gln
305                 310                 315                 320

Val Phe Leu Asp Arg Thr His Ser Gly Ile Val Ser Phe Asp Lys Thr
                325                 330                 335

Phe Pro Thr Val Tyr Asn Thr Thr Leu Ala Pro Cys Ser Asp Gly Glu
            340                 345                 350

Val Arg Leu Gln Leu Leu Val Asp Trp Ser Ser Val Glu Val Phe Gly
            355                 360                 365

Gly Glu Gly Glu Lys Thr Val Thr Ala Gln Ile Phe Pro Asn Glu Glu
            370                 375                 380

Ala Thr His Val Glu Leu Phe Ser Thr Gly Gly Ser Thr Gly Asn Val
385                 390                 395                 400

Lys Val Glu Ile Trp Asp Val Ser Ser Ile Trp Asn
                405                 410

<210> SEQ ID NO 12
<211> LENGTH: 543
<212> TYPE: PRT
<213> ORGANISM: Penicillium restrictum A191

<400> SEQUENCE: 12

Met Leu Lys Phe Ala Ser Ala Phe Val Leu Gly Leu Ala Gly Pro
 1               5                  10                  15

Thr Val Ala Val Asn Tyr Thr Glu Pro Phe Arg Pro Gln Tyr His Phe
            20                  25                  30

Ser Pro Ala Lys His Trp Thr Asn Asp Pro Ala Gly Leu Phe Tyr Tyr
            35                  40                  45

Asp Gly Thr Tyr His Met Phe Phe Gln Tyr Asn Pro Gly Gly Ile Glu
            50                  55                  60

Trp Gly Asn Met Ser Trp Gly His Ala Thr Ser Lys Asp Leu Thr His
65                  70                  75                  80

Trp Asp Glu Gln Pro Val Ala Leu Leu Ala Lys Gly Tyr Pro Asn Asn
                85                  90                  95

Val Thr Glu Met Tyr Phe Thr Gly Ser Ala Val Ala Asp Val Asn Asn
            100                 105                 110

Thr Ser Gly Phe Gly Thr Asp Gly Lys Val Pro Leu Val Ala Ile Tyr
            115                 120                 125

Thr Ser Tyr Tyr Thr Val Thr Gln Thr Leu Pro Ser Gly Lys Arg Val
```

```
                130              135             140
His Lys Asp Gln Gln Ser Gln Ser Ile Ala Tyr Ser Leu Asp Asn Gly
145                 150                 155                 160

Met Thr Trp Thr Pro Tyr Asp Ser Val Asn Pro Val Ile His Tyr Pro
                165                 170                 175

Pro Pro Pro Tyr His Ser Gln Tyr Lys Asn Phe Arg Asp Pro Phe Val
            180                 185                 190

Phe Trp His Asp Gln Thr Gln Arg Trp Ile Leu Val Thr Thr Leu Ala
        195                 200                 205

Glu Leu His Lys Leu Val Ile Trp Thr Ser Asp Asn Leu Lys Asp Trp
    210                 215                 220

Thr Val Leu Ser Glu Phe Gly Pro Tyr Asn Gly Val Gly Gly Val Trp
225                 230                 235                 240

Glu Cys Pro Asn Leu Phe Pro Leu Pro Val Asp Gly Asp Gly Asp Glu
                245                 250                 255

Asn Met Thr Lys Trp Val Met Val Val Gly Leu Asn Pro Gly Gly Pro
            260                 265                 270

Pro Gly Thr Val Gly Ser Gly Thr Gln Tyr Phe Ile Gly Asn Phe Asn
        275                 280                 285

Gly Thr Ala Phe Ile Pro Asp Ala Asp Thr Ile Tyr Pro Gly Asn Lys
    290                 295                 300

Thr Ala Asn Trp Met Asp Trp Gly Pro Asp Phe Tyr Ala Ala Ala Ala
305                 310                 315                 320

Tyr Asn Gly Leu Pro Lys Glu Asp His Val Gln Leu Ala Trp Met Asn
                325                 330                 335

Asn Trp Gln Tyr Gly Glu His Ile Pro Thr His Pro Trp Arg Ser Ala
            340                 345                 350

Met Ala Ile Pro Arg His Leu Ser Leu Lys Asn Ile Asp Ser Lys Thr
        355                 360                 365

Thr Leu Val Gln Gln Pro His Val Asn Trp Lys Ser Ile Lys Gly Lys
    370                 375                 380

His Ala Tyr Thr Arg Phe Trp Lys Ser Val Asp Glu Gly Ile Thr Asp
385                 390                 395                 400

Leu Gly Pro Leu Gly Lys Thr Leu Ala Ile Asp Ile Thr Phe Ser Thr
                405                 410                 415

Pro Lys Asp Ala Gly Ser Gln Thr Phe Gln Phe Gly Ile Val Val Gln
            420                 425                 430

Ala Thr Glu Asp Leu Ser Gln His Thr Arg Val Gly Tyr Asp Phe Gln
        435                 440                 445

Ser Gln Gln Val Phe Leu Asp Arg Thr His Ser Gly Ile Val Ser Phe
    450                 455                 460

Asp Lys Thr Phe Pro Thr Val Tyr Asn Thr Thr Leu Ala Pro Cys Ser
465                 470                 475                 480

Asp Gly Glu Val Arg Leu Gln Leu Leu Val Asp Trp Ser Ser Val Glu
                485                 490                 495

Val Phe Gly Gly Glu Gly Glu Lys Thr Val Thr Ala Gln Ile Phe Pro
            500                 505                 510

Asn Glu Glu Ala Thr His Val Glu Leu Phe Ser Thr Gly Gly Ser Thr
        515                 520                 525

Gly Asn Val Lys Val Glu Ile Trp Asp Val Ser Ser Ile Trp Asn
    530                 535                 540
```

<210> SEQ ID NO 13

<211> LENGTH: 524
<212> TYPE: PRT
<213> ORGANISM: Penicillium restrictum A191

<400> SEQUENCE: 13

```
Val Asn Tyr Thr Glu Pro Phe Arg Pro Gln Tyr His Phe Ser Pro Ala
  1               5                  10                  15

Lys His Trp Thr Asn Asp Pro Ala Gly Leu Phe Tyr Tyr Asp Gly Thr
             20                  25                  30

Tyr His Met Phe Phe Gln Tyr Asn Pro Gly Gly Ile Glu Trp Gly Asn
         35                  40                  45

Met Ser Trp Gly His Ala Thr Ser Lys Asp Leu Thr His Trp Asp Glu
     50                  55                  60

Gln Pro Val Ala Leu Leu Ala Lys Gly Tyr Pro Asn Asn Val Thr Glu
 65                  70                  75                  80

Met Tyr Phe Thr Gly Ser Ala Val Ala Asp Val Asn Asn Thr Ser Gly
                 85                  90                  95

Phe Gly Thr Asp Gly Lys Val Pro Leu Val Ala Ile Tyr Thr Ser Tyr
            100                 105                 110

Tyr Thr Val Thr Gln Thr Leu Pro Ser Gly Lys Arg Val His Lys Asp
        115                 120                 125

Gln Gln Ser Gln Ser Ile Ala Tyr Ser Leu Asp Asn Gly Met Thr Trp
130                 135                 140

Thr Pro Tyr Asp Ser Val Asn Pro Val Ile His Tyr Pro Pro Pro
145                 150                 155                 160

Tyr His Ser Gln Tyr Lys Asn Phe Arg Asp Pro Phe Val Phe Trp His
                165                 170                 175

Asp Gln Thr Gln Arg Trp Ile Leu Val Thr Thr Leu Ala Glu Leu His
            180                 185                 190

Lys Leu Val Ile Trp Thr Ser Asp Asn Leu Lys Asp Trp Thr Val Leu
        195                 200                 205

Ser Glu Phe Gly Pro Tyr Asn Gly Val Gly Val Trp Glu Cys Pro
    210                 215                 220

Asn Leu Phe Pro Leu Pro Val Asp Gly Asp Gly Asp Glu Asn Met Thr
225                 230                 235                 240

Lys Trp Val Met Val Val Gly Leu Asn Pro Gly Gly Pro Pro Gly Thr
                245                 250                 255

Val Gly Ser Gly Thr Gln Tyr Phe Ile Gly Asn Phe Asn Gly Thr Ala
            260                 265                 270

Phe Ile Pro Asp Ala Asp Thr Ile Tyr Pro Gly Asn Lys Thr Ala Asn
        275                 280                 285

Trp Met Asp Trp Gly Pro Asp Phe Tyr Ala Ala Ala Tyr Asn Gly
    290                 295                 300

Leu Pro Lys Glu Asp His Val Gln Leu Ala Trp Met Asn Asn Trp Gln
305                 310                 315                 320

Tyr Gly Glu His Ile Pro Thr His Pro Trp Arg Ser Ala Met Ala Ile
                325                 330                 335

Pro Arg His Leu Ser Leu Lys Asn Ile Asp Ser Lys Thr Thr Leu Val
            340                 345                 350

Gln Gln Pro His Val Asn Trp Lys Ser Ile Lys Gly Lys His Ala Tyr
        355                 360                 365

Thr Arg Phe Trp Lys Ser Val Asp Glu Gly Ile Thr Asp Leu Gly Pro
    370                 375                 380

Leu Gly Lys Thr Leu Ala Ile Asp Ile Thr Phe Ser Thr Pro Lys Asp
```

```
385                 390                 395                 400
Ala Gly Ser Gln Thr Phe Gln Phe Gly Ile Val Val Gln Ala Thr Glu
                405                 410                 415

Asp Leu Ser Gln His Thr Arg Val Gly Tyr Asp Phe Gln Ser Gln Gln
                420                 425                 430

Val Phe Leu Asp Arg Thr His Ser Gly Ile Val Ser Phe Asp Lys Thr
                435                 440                 445

Phe Pro Thr Val Tyr Asn Thr Thr Leu Ala Pro Cys Ser Asp Gly Glu
            450                 455                 460

Val Arg Leu Gln Leu Leu Val Asp Trp Ser Ser Val Glu Val Phe Gly
465                 470                 475                 480

Gly Glu Gly Glu Lys Thr Val Thr Ala Gln Ile Phe Pro Asn Glu Glu
                485                 490                 495

Ala Thr His Val Glu Leu Phe Ser Thr Gly Ser Thr Gly Asn Val
            500                 505                 510

Lys Val Glu Ile Trp Asp Val Ser Ser Ile Trp Asn
            515                 520

<210> SEQ ID NO 14
<211> LENGTH: 306
<212> TYPE: PRT
<213> ORGANISM: Penicillium restrictum A191

<400> SEQUENCE: 14

Met Arg Ala Val Gln Glu Asp Leu Leu Thr Leu Glu Ile Ile Pro Asp
  1               5                  10                  15

Ser Arg Val Leu Gly Gln Val Phe Arg Gly Leu Asp Asp Ser Glu
                 20                  25                  30

Leu Lys Gly Leu Arg Thr Ser Val Leu Gly Arg Gly Lys Gly Tyr Ile
                 35                  40                  45

Asp Cys Lys Cys Leu Ala Gln Arg Ser Glu Val Cys Asp Ala Phe Val
             50                  55                  60

Asp Thr Leu Pro Glu Ala Gly Val Ser Met Leu Ala Leu Asp Arg Phe
65                  70                  75                  80

Pro Val His Val Trp Leu Leu Asp Glu Ser Arg Leu Arg Val Asp Val
                 85                  90                  95

Leu Gln Arg Gln Val Thr Arg Asp Ser His Arg Ala Ser Pro Gly Val
                100                 105                 110

Ser Arg Asp Met Phe Thr Ile Leu Pro Val Ile His Pro Cys Glu Leu
                115                 120                 125

Asp Met Val Leu Leu Arg Glu Thr Val Val Ser Gly Ser Ser Val Glu
            130                 135                 140

Val Arg Ala Pro Val His Pro Val Gly Ser Leu Val Ser Gly Val Asp
145                 150                 155                 160

Gly Ile Gly Ile Arg Asn Lys Gly Cys Ala Ile Glu Val Ala Asp Lys
                165                 170                 175

Val Leu Cys Ser Gly Thr Asp Ser Thr Arg Trp Ser Ala Gly Val Glu
                180                 185                 190

Ser Asn Asp His Asp Pro Leu Gly His Val Leu Val Thr Val Thr Val
                195                 200                 205

Asn Trp Lys Arg Glu Glu Val Gly Ala Leu Pro His Thr Pro Asp Ala
            210                 215                 220
```

```
Ile Val Gly Ala Glu Phe Ala Glu Asp Gly Pro Val Leu Glu Ile Val
225                 230                 235                 240

Gly Cys Pro Asp His Glu Leu Val Gln Phe Ser Gln Gly Gly Asp Glu
            245                 250                 255

Asn Pro Ser Leu Gly Leu Val Val Pro Glu His Glu Arg Val Thr Glu
            260                 265                 270

Val Leu Val Leu Ala Val Val Gly Arg Gly Arg Val Val Asp His Arg
            275                 280                 285

Val Asp Arg Val Val Arg Cys Pro Cys His Ala Ile Val Gln Thr Val
        290                 295                 300

Gly Asn
305

<210> SEQ ID NO 15
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 15
tccaccatgg tcaagtttgc gagcgccttc g                              31
```

ENZYME OR CELL PREPARATION WITH INULINASE ACTIVITY

CROSS-REFERENCE TO RELATED APPLICATIONS

This application claims priority to European Application Serial No. EP 00870264.9, filed Nov. 9, 2000, the disclosure of which is herein incorporated by reference in its entirety.

BACKGROUND OF THE INVENTION

1. Field of the Invention

The present invention relates to enzyme or cell preparations with inulinase activities from *Penicillium restrictum*, to their obtention and to their use in the hydrolysis of fructan polymers.

2. Description of the Related Art

Inulin is a polydisperse composition made of oligo- and polysaccharides which are composed of fructose units linked together by β(2-1) linkages. Most molecules are terminated by a glucose unit. They can be hydrolyzed into monomers by acidic treatment (pH 1-2) for 1 to 2 hours at high temperature. However, undesirable secondary products may appear during this process, leading to a lower yield.

A known alternative to this process is the enzymatic hydrolysis. Enzymes preparations obtained from cultures of various micro-organisms have been described to hydrolyze inulin. Among these are the yeasts *Kluyveromyces marxianus*, Debaromyces, *Candida kefyr*, the molds *Aspergillus oryzae*, *Aspergillus ficuum*, *Fusarium oxysporum* and some bacterial species from the genus Actinomyces or Lactobacillus. There are also some plants that synthesize inulinases.

Some parameters are required for an economical and realistic industrial process of inulin hydrolysis:

The working temperature needs to be high (above 60° C.) (required to achieve an adequate level of inulin concentration in the solution to be treated, but minimizes also microbial infections).

The working pH should be slightly acidic (pH 4-6) to keep a good stability of the fructose reaction product.

The enzyme preparation should be stable in the working conditions.

The hydrolysis of the inulin should be as complete as possible, giving at least 98% of glucose and fructose yield on a dry weight basis.

The enzyme preparation should work in concentrated inulin solution (20% and higher).

It is therefore highly desirable to have an improved inulinase preparation and that preferably presents the following characteristics:

optimal temperature above 60° C., preferably at about 65° C.

optimal pH between about 4.0 and about 6.0.

high stability in working conditions.

achievement of a complete hydrolysis.

substrate concentration of about 20% or higher.

Another aim of the present invention is related to the use of said enzyme preparation, preferably in the absence of cells or cell debris, preferably in the form of extracellular medium comprising most of the enzymatic activity of said inulinase, for the enzymatic treatment of inulin and inulin containing materials or the synthesis of fructose oligomers.

SUMMARY OF THE INVENTION

The present invention is related to an isolated and purified enzyme with inulinolytic activity having more than 75% sequence identity with the amino acid sequence SEQ ID NO 12 to its encoding nucleotide sequence to a cell producing the enzyme and to the use for the degradation of inulin or inulin-containing plant material, especially for the production of fructose syrups and for the production of oligomers of fructose.

Some embodiments of the present invention are described in the following numbered paragraphs:

Paragraph 1: An isolated and purified enzyme with inulinolytic activity having more than 75% sequence identity with the amino acid sequence SEQ ID NO 12.

Paragraph 2: The enzyme according to paragraph 1, having more than 80% sequence identity with the amino acid sequence SEQ ID NO 12.

Paragraph 3: An isolated and purified enzyme amino acid sequence having the amino acid sequence of SEQ ID NO 12 or a portion thereof having an inulinolytic activity.

Paragraph 4: The enzyme according to paragraph 1, which presents an optimum enzymatic activity at a pH between about 4.0 and about 6.0 and at a temperature between about 60 and about 70° C.

Paragraph 5: An isolated and purified nucleotide sequence encoding the enzyme according to paragraph 1, 3 or 4.

Paragraph 6: An isolated and purified nucleotide sequence which encodes a polypeptide having a inulinolytic activity and has more than 75% sequence identity with the nucleotide sequence SEQ ID NO 9.

Paragraph 7: The isolated and purified nucleotide according to paragraph 6, which has more than 80% sequence identity with the nucleotide sequence SEQ ID NO 9.

Paragraph 8: An isolated and purified nucleotide sequence SEQ ID NO 9 or a portion thereof encoding a polypeptide having an inulinolytic activity.

Paragraph 9: A recombinant nucleotide sequence comprising, operably linked to the nucleotide sequence according to paragraph 5, one or more adjacent regulatory sequence(s), preferably originating from homologous microorganisms.

Paragraph 10: A vector comprising the nucleotide sequence according to paragraph 5.

Paragraph 11: The vector according to paragraph 10, being a plasmid incorporated in *Escherichia coli* and having the deposit number LMBP-4252.

Paragraph 12: A cell producing the enzyme according to paragraph 1.

Paragraph 13: The cell of paragraph 12, having a deposit number MUCL-42612.

Paragraph 14: The cell according to the paragraph 12 being a recombinant host cell transformed by the nucleotide sequence according to paragraph 5 or the vector according to paragraph 10 or 11.

Paragraph 15: The recombinant host cell according to paragraph 14, which is selected from the group consisting of bacteria or fungi, including yeast.

Paragraph 16: The cell according to any one of the preceding paragraphs 12 to 15, wherein the enzyme is extra-cellularly expressed by said cell.

Paragraph 17: The cell according to paragraph 12, wherein the enzyme is intra-cellularly expressed by said cell.

Paragraph 18: A solid support fixing an element selected from the group consisting of the cell according to paragraph 12, a cell extract of the cell according to paragraph 12 and/or the isolated and purified enzyme with inulinolytic activity according to paragraph 1.

Paragraph 19: A method for the degradation of inulin or inulin-containing plant material by the addition of the recombinant host cell according to paragraph 12 or the enzyme with inulinolytic activity according to paragraph 1.

BRIEF DESCRIPTION OF THE DRAWINGS

FIG. 5 shows the complete genetic sequence of the inulinase according to the present invention.

DETAILED DESCRIPTION OF THE PREFERRED EMBODIMENT

Figure 1:
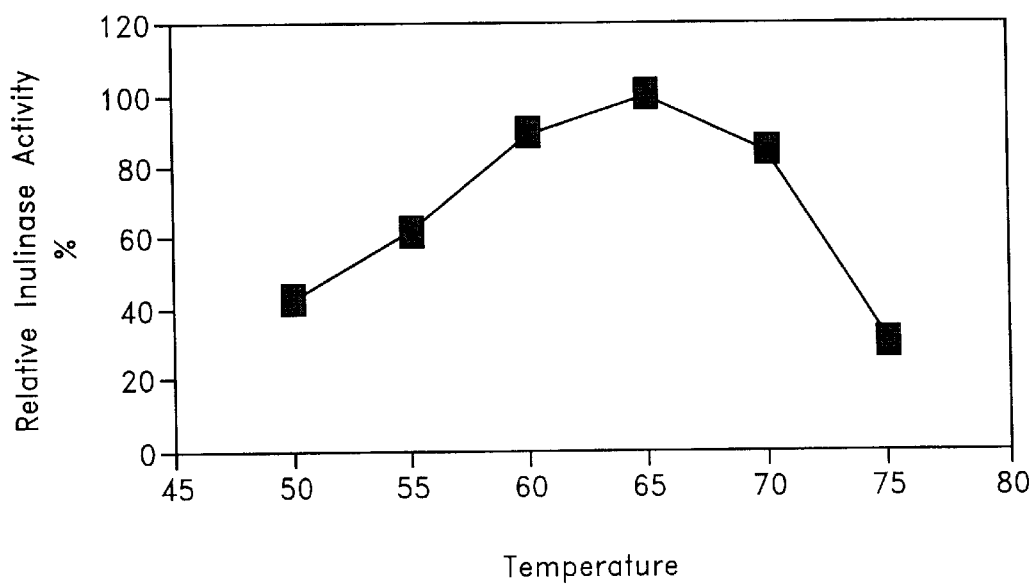
FIG. 1 shows the effect of the temperature on the *Penicillium restrictum* A191 inulinase activity.

The present invention is related to a new strain of *Penicillium restrictum* isolated, purified and characterized by the inventors, namely *Penicillium restrictum* A191, which produces an improved enzyme preparation with inulinase activity that presents advantageously the above-mentioned properties. This strain has been deposited in the MUCL ("Mycothèque de l'Université Catholique de Louvain") under the accession number MUCL 42612.

The inulinase preparation from *Penicillium restrictum* A191, may be obtained by culturing the strain in a suitable culture medium.

Such medium may be, for example, the MRI medium. MRI medium is composed of casein peptone (1%), yeast extract (1%) and inulin (1.5%). Other media like the well-known Czapeck medium may be used accordingly, provided that it is supplemented with inulin as carbon source.

In a preferred embodiment of this invention, the strain is grown in a fermenter in controlled conditions such as pH control, temperature control, dissolved oxygen control, etc.

After culture for a period between 3 to 9 days, the enzyme preparation may be recovered from the extracellular culture medium. The enzyme preparation may be further purified using techniques known in the art such as chromatography, dialysis, etc.

Alternatively or in addition, the enzyme preparation may be treated to obtain a product under the desired form. Such treatments may include (but are not restricted to) concentration and/or diafiltration by ultrafiltration, drying by freeze-drying or spray-drying or evaporation or a combination of these techniques. Thereafter, the final product may be recovered either in a liquid or a solid form.

A further aspect of the present invention is related to an isolated and purified (from possible contaminants) inulinase amino acid sequence possibly glycosylated presenting more than 75%, preferably more than 80 or 85%, more preferably more than 90% or 95% sequence identity (or homology) with the amino acid sequence SEQ ID NO 12.

Said inulinase amino acid sequence or peptide possibly glycosylated is preferably extracellularly or intracellularly expressed and/or secreted by a recombinant host cell according to the invention and described hereafter.

According to a preferred embodiment of the present invention, the isolated and purified inulinase amino acid sequence possibly glycosylated has the amino acid sequence of SEQ ID NO 12 or a smaller active portion of said amino acid sequence (of more than 30 or 50 amino-acids, preferably more than 100 amino-acids), which present at least more than 80% of the inulinase activity of the complete amino-acid sequence SEQ ID NO 12 (preferably more than 95% of the inulinase activity of the complete inulinase activity of the complete amino-acid sequence SEQ ID NO 12). In other words, the isolated and purified inulinase amino acid sequence according to the invention may be deleted partially, while maintaining its enzymatic activity, which may be measured upon specific substrate by methods well known by the person skilled in the art.

The purified complete inulinase enzyme according to the invention is also characterized by a molecular weight of about 70–75 kD optimum pH around pH 5.0 and a temperature profile having its maximum activity at about 65° C. More generally, the maximum activity of the enzyme is comprised between pH 4.0 and 6.0, at a temperature comprised between 55 to 70° C. (see enclosed FIG. 1).

The optimum temperature is advantageously higher than those described in the available literature. The maximal activities of the *Aspergillus ficuum* (Ettalibi et al, 1990, Agric. Biol. Chem., vol 54, p.61), *Aspergillus phoenicis* (EP application 0043169), *Penicillium janczewskii* (Pessoni et al, 1999, J. Appl. Microbiol., vol 87, p. 141) inulinases are respectively 60° C., 60° C., and 55° C. Yeast and bacterial inulinases display generally a lower optimal temperature. See also the reviews of Vandamme & al (1983, Adv. Appl. Microbiol., vol 29, p. 139) and of Pandey & al (1999, Appl. Biochem. Biotechnol., vol 81, p. 35).

Figure 2:
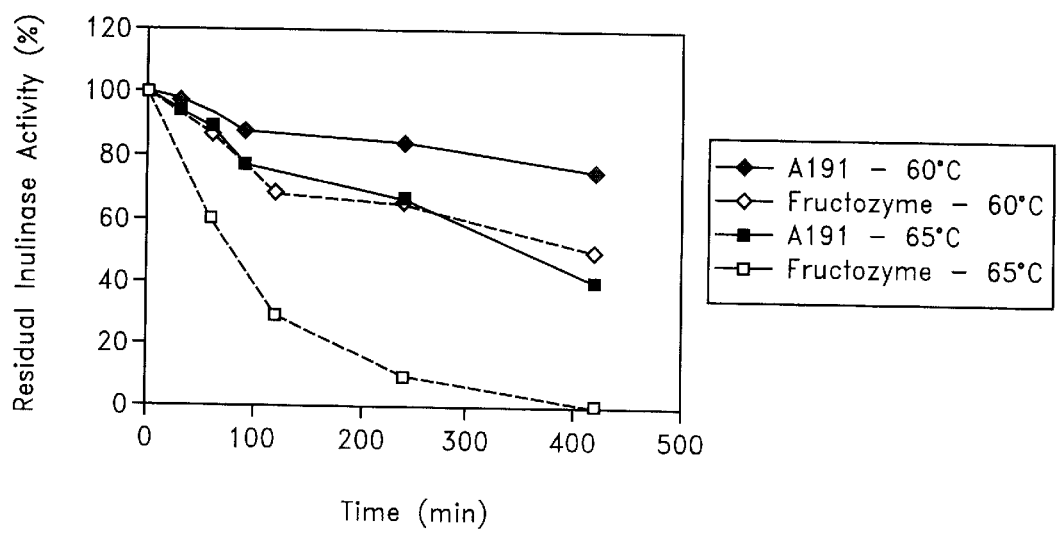
FIG. 2 shows the residual activity of the inulinase preparation after preliminary heat treatment.

Moreover the inulinase of the present invention retains more than 80% of its activity after being preincubated in diluted conditions at 60° C. for 240 min, and more than 65% of its activity after being preincubated in diluted conditions at 65° C. for 240 min (see FIG. 2).

The present invention is also related to an isolated and purified nucleotide sequence from a micro-organism origin, encoding the inulinase according to the invention. Preferably, said micro-organism is selected from the group consisting of bacteria or fungi (including yeast), preferably the Penicillium species fungi, more preferably the *Penicillium restrictum*.

According to a preferred embodiment of the present invention, said micro-organism is *Penicillium restrictum* A191 having the deposit number MUCL 42612.

According to the invention, said nucleotide sequence presents more than 75%, preferably more than 80%, more preferably more than 90% or 95% sequence identity (or homology) with the sequence SEQ ID NO 9 described hereafter.

According to a preferred embodiment of the present invention, said isolated and purified nucleotide sequence corresponds to the nucleotide sequence SEQ ID NO 9 or an active portion thereof encoding a peptide having a inulinase activity.

It is meant by "an active portion of the nucleotide sequence SEQ ID NO 9", a fragment of said sequence SEQ ID NO 9 having more than 90 nucleotides, preferably more than 100 nucleotides or more than 120 nucleotides, of said nucleotide sequence and encoding a protein characterized by an inulinase enzymatic activity similar to the inulinase activity of the complete amino-acid sequence SEQ ID NO 12. Preferably, said portion has a inulinase enzymatic activity corresponding to more than 80% of the initial inulinase enzymatic activity of the complete enzyme defined by its amino-acid sequence SEQ ID NO 12, preferably has a inulinase enzymatic activity corresponding to the one of the amino acid sequence SEQ ID NO 12.

Another aspect of the present invention is related to a recombinant nucleotide sequence comprising, operably linked to the nucleotide sequence according to the invention and above-described, one or more adjacent regulatory sequence(s), preferably originating from homologous micro-organisms.

However, said adjacent regulatory sequences may also be originating from heterologous micro-organisms.

These adjacent regulatory sequences are specific sequences such as promoter sequences, secretion signal sequences and terminator sequences.

Another aspect of the invention is related to the vector comprising the nucleotide sequence(s) originating from homologous or from heterologous micro-organisms.

It is meant by "a vector", any biochemical construct which may be used for the introduction of a nucleotide sequence (by transduction, transfection, transformation, infection, conjugation, etc) into a target cell. Advantageously, the vector according to the invention is selected from the group consisting of plasmids, viruses, phagemids, chromosomes, transposons, liposomes, cationic vesicles or a mixture thereof. Said vector may comprise already one or more of the above-described adjacent regulatory sequence(s) (able to allow its expression and its transcription into a corresponding peptide by said cell). Preferably, said vector is a plasmid incorporated in *Escherichia coli* and having the deposit number LMBP 4252.

The present invention is also related to the host target cell, preferably a recombinant host cell, "transformed" by the nucleotide sequence or the vector above-described, which means by a cell having incorporated said nucleotide sequence or said vector and which does not comprise naturally (originally) said nucleotide sequence. The transformed host cell may be also a cell having incorporated said vector or said nucleotide sequence by genetic transformation, preferably by homologous recombination or other method.

Preferably, said host cell is also capable of overexpressing (higher expression than the expression observed in the initial cell) said nucleotide sequence or said vector and allows advantageously a high production of an amino acid sequence encoded by said nucleotide sequence or by said vector. The isolated and purified nucleotide sequence according to the invention may be either integrated into the genome of the selected host cell or present on an episomal vector in said host cell.

Advantageously, the recombinant host cell according to the invention is selected from the group consisting of the microbial world, preferably bacteria or fungi, including yeast.

Preferably, said recombinant host cell is modified to obtain an expression of the inulinase enzyme at high level obtained by the use of adjacent regulatory sequences being capable of directing the overexpression of the nucleotide sequence according to the invention in the recombinant host cell or by increasing the number of copies of the nucleotide sequences according to the invention.

The following description describes also the conditions (culture media, temperature and pH conditions, etc) for the culture of the host selected for the expression of the inulinase according to the invention. For this purpose, the original production species and/or a suitable host cell transformed with a DNA construct designed to express the said enzyme are present in a suitable growth medium.

According to the present invention, said protein with inulinolytic activity may be isolated from the medium and/or purified (culture, isolation and purification conditions are derived from conventional methods well-known to person skilled in the art).

The new strain, or the enzymatic preparation with inulinase activity according to the present invention may be used for the treatment of inulin-containing materials (such as, but not restricted to chicory roots, dahlia tubers or jerusalem artichokes). In particular, the said preparation shows a hydrolytic activity in the presence of inulin-containing material. More particularly the said preparation may be used for the production of high-fructose syrups.

Another application of the enzymatic preparation with inulinase activity according to the present invention is the obtention of oligomers of fructose by incomplete hydrolysis of inulin. Oligomers of fructose with various chain length derived from the partial hydrolysis of the inulin are food and/or feed ingredients that are used for example as dietary fiber, prebiotic, low caloric products.

A further application of the enzymatic preparation with inulinase activity according to the present invention is the synthesis of fructose oligomers starting from low molecular weight saccharides such as sucrose.

The effect of the enzyme with inulinolytic activity of the present invention may be further improved by adding other enzymes in combination with said enzyme. Such enzymes may belong (but are not restricted) to hydrolytic enzymes families such as glucanases, proteases, cellulases, hemicellulases or pectinases. Other enzymes are transglutaminases, oxido-reductases, isomerases, etc.

The enzyme with inulinolytic activity according to the invention may be used under several forms. The strain MUCL 42612 or recombinant cells expressing the enzyme, such as yeast, fungi, archeabacteria or bacteria, may be used directly in an industrial or experimental process.

Said enzyme preparation may be used as a cell extract, a cell-free extract (i.e. portions of the cell that has been submitted to one or more disruption, centrifugation and/or extraction steps) or as a purified protein. Any of the above-described forms may be used in combination with one or more enzyme(s) under any of the above-described forms. These whole cells, cell extracts, cell-free extracts, enzyme preparations or purified enzymes may be immobilized by any conventional mean on a solid support to allow protection of the enzyme, continuous hydrolysis of substrate and/or recycling of the enzymatic preparation. Said cells, cells extracts, cell-free extracts, enzyme preparations or purified enzymes may be mixed with different ingredients, e.g. in the form of a dry powder or a granulate, in particular a non-dusting granulate, in a form of a liquid, for example with stabilizers such as polyols, sugars, organic acids, sugar alcohols according to well-established methods.

The invention will be described in further details in the following examples by reference to the drawings, which are not in any way intended to limit the scope of the invention as claimed.

EXAMPLES

Example 1
Isolation of an Inulinase-producing Strain
Inulinase Assay

The inulinase activity was determined by measuring the release of reducing sugars from inulin using the dinitrosalicylic acid method (MILLER, 1959, Anal. Chem., vol 31, p. 426). The substrate used was inulin from Dahlia obtained from Sigma at a final concentration of 5%. Fructose was used as standard. One unit of inulinase is defined as the amount of enzyme which released 1 μmole of fructose per minute in the assay conditions.

Strain Isolation 5 grams of a soil sample from Belgium were suspended in 50 ml of a saline solution (NaCl 0.9%). After appropriate dilutions, aliquots were spread onto PDA plates (Potato Dextrose Agar 3.9%—Difco Laboratories) supplemented with 100 μg/ml of ampicillin.

After growth at 30° C., the emerging colonies were re-isolated on individual plates and replicated onto MRI plates (casein peptone 1%, yeast extract 1%, inulin from Dahlia 1.5%, agar 1.5%). The strains that gave an inulin hydrolysis halo around the colonies were cultivated in liquid MRI. Extracellular enzymes were further characterized with regard to the properties of the inulinase activity. A strain exhibiting an inulinase activity with a high optimum temperature and a pH optimum around 5.0 was retained. This strain, with the reference number A191, was identified as *Penicillium restrictum*. It has been deposited on Feb. 18, 2000 in the BCCM/MUCL (Mycothèque de l'Université Catholique de Louvain, Université Catholique de Louvain, Place Croix du Sud, 3, B-1348 Louvain-la-Neuve, Belgium) under the accession number MUCL 42612.

Example 2
Inulinase Production and Characterization
Inulinase Production

Spores of *Penicillium restrictum* A191 were obtained by culturing the strain on PDA medium (Potato Dextrose Agar—DIFCO). Two 3 days-old 250 ml cultures were used to inoculate a 20 1 fermentor (Biolafitte). The culture medium was the following: casein peptone 1%, Yeast extract 1% and inulin 1.5%. The fermentation parameters were the following : temperature 30° C., Aeration 1 vvm, agitation 200 rpm. The initial pH was 5.8 and was not controlled during the fermentation. After 120 hours, the culture supernatant was separated from the cells by centrifugation.

Optimal Temperature and pH

The optimal temperature of the inulinase was determined by measuring the activity at various temperatures and was found to be around 65° C. (FIG. 1). The enzyme retains more than 80% of its activity in the range 60 to 70° C.

The optimal pH for the inulinase activity is around pH 5.0.

Stability

The stability of the enzyme in diluted conditions has been evaluated by preincubation at 60° C. and 65° C. and compared to a commercial inulinase preparation (Fructozym™—Novo Nordisk A/S). The results of a typical experiment are presented in FIG. 2.

Example 3
Inulin Hydrolysis

Figure 3:
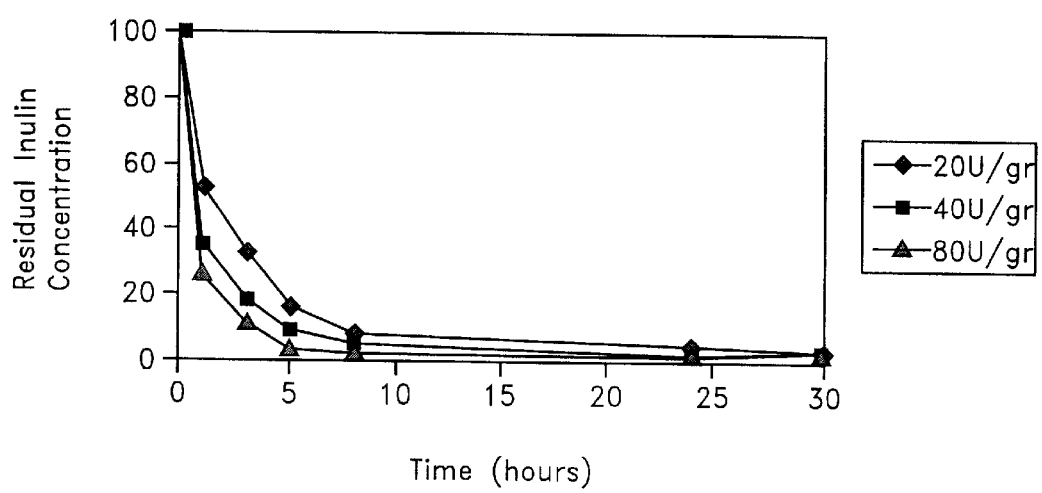
FIG. 3 shows the residual inulin amount after hydrolysis with the Penicillium restrictum A191 inulinase.

The ability of the *Penicillium restrictum* A191 inulinase preparation to hydrolyze inulin has been tested by incubating a 25% inulin solution at 65° C. and pH 5.0 with increasing concentrations of the enzyme. The residual inulin concentration has been determined by HPLC using a Supelcogel Ca column™ (Supelco) to separate the mono and di-saccharides from the higher oligosaccharides. The concentration was expressed as the percentage of the residual oligosaccharides peak area compared to untreated inulin. The FIG. 3 shows that the inulinase of the present invention could hydrolyze completely the inulin solution. The residual percentage is due to non-inulin contaminating material present in the inulin solution.

The overall performance of the A191 strain of *Penicillium restrictum* compared to a commercial product (Fructozym™—Novo Nordisk) and a publicly available *Penicillium restrictum* strain (CBS 367 48) has been demonstrated by comparing the hydrolysis of a 20% inulin solution at 65° C. and at pH 5.0 for 24 and 48 hours using 5.7 inulinase units/gr of inulin. The results of a typical experiment are shown on the following table.

| | Residual inulin concentration (%) | | |
|---|---|---|---|
| | A191 | Fructozym ™ | CBS36748 |
| 0 h | 100 | 100 | 100 |
| 24 h | 10.0 | 11.3 | 68.1 |
| 48 h | 4.3 | 8.2 | 70.6 |

Example 4
Purification of the Inulinolytic Enzyme of *Penicillium restrictum* A 191

*Penicillium restrictum* A191 was cultivated at 30° C. in 2 liters of Aspergillus Minimal Medium (Ponteverco et al., 1953, Adv. Genet.; vol 5, p. 142), adjusted at pH 6.5 and supplemented with 1% inulin from chicory root (Sigma). After 72 hours, the culture was filtered through a Miracloth filter (Calbiochem) to remove the mycelium. The filtrate was concentrated by ultrafiltration in a Pellicon device with a 10 kDa Biomax 10 cassette (Millipore) to a final volume of 100 ml. The concentrate was desalted on a Pharmacia Hiprep 26/10 desalting column™ using as eluent a 50 mM sodium acetate buffer containing 10 mM NaCl (pH 4.3).

This solution was loaded at 2 ml/min on a Pharmacia XK16/20 column™ filled with 30 ml of Bio-Rad Macro High S resin equilibrated in 50 mM sodium acetate pH 4.3. Proteins were eluted with a linear increasing NaCl gradient from 0 to 1 M NaCl in 50 mM sodium acetate buffer pH 4.4. Inulinase activity was determined in the eluted fractions. 45% of the inulinase activity loaded on the column was recovered in one peak. Active fractions were pooled and equilibrated in 1.3 M ammonium sulfate, 50 mM Na acetate pH 4.88 in a final volume of 9 ml.

These fractions were applied on a Phenyl Sepharose HP column™ (Pharmacia) and eluted at 2.5 ml/min with a 1.3M-0M ammonium sulfate linear gradient in a 50 mM Na acetate buffer pH 4.88. Inulinase activity was determined in the eluted fractions. The inulinase activity was collected as one peak whose conductivity was around 145 mS/cm.

Figure 4:
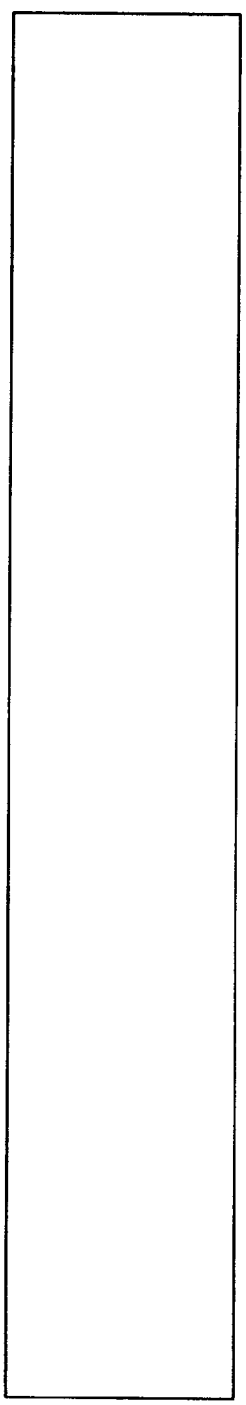
FIG. 4 shows a SDS-polyacrylamide gel of the proteins recovered after the successive purification steps of the enzyme with inulinolytic activity.

One major protein was present in this peak as shown by SDS-polyacrylamide gel (FIG. 4).

Example 5
Determination of the Amino Acid Sequence of the Enzyme with the Inulinolytic Activity General procedures were followed to perform the N-terminal sequencing of the protein purified as in Example 4 after electrophoresis on a 12% SDS-polyacrylamide gel and electroblotting on a PVDF Immobilon-P membrane™ (Millipore). An automatic 477A Protein Sequencer coupled to a HPLC 120A Analyser (Applied Biosystem) was used.

The following sequence (SEQ ID NO 1) has been obtained with the N-terminal sequencing of the protein with an apparent molecular weight of 77 kDa:

SEQ ID NO 1:

L(G)YTEPYR(P-G)QYTF(S)PDQEN(V)(M)

For the determination of the sequence of an internal fragment, the protein was first digested on the membrane with trypsine. The resulting peptides were separated by reverse phase chromatography on HPLC, and subjected to N-terminal sequencing as described above. The following internal. sequence has been obtained:

SEQ ID NO 2:

DLTHWDEQPVA

Example 6

Cloning of a Gene Coding for an Enzyme with Inulinolytic Activity

Cloning of an Internal DNA Fragment

The genomic DNA (gDNA) from *Penicillium restrictum* A191 was isolated according to Boel et al. (EMBO J., 1984, vol 7, p. 1581). The strain was grown in 50 ml Aspergillus Minimum Medium supplemented with 0.5% Yeast Extract (Difco). After 24 hours, the mycelium was harvested by filtration on a Miracloth filter and washed twice with water. 1 g mycelium was incubated in 10 ml solution A (sorbitol 1 M, EDTA 25 mM, pH 8.0) for 30 min at 30° C. The cells were then centrifuged and suspended in 10 ml solution B (Novozym 234 20 mg, sorbitol 1 M, Na citrate 0.1 M, EDTA 10 mM, pH 5.8). After 30 min at 30° C., the cells were centrifuged and lysed with 15 ml of solution C (phenol 40%, SDS 1%). DNA was separated from the contaminating material by successive extractions with phenol and phenol-chloroform, followed by ethanol precipitation.

The degenerated synthetic oligonucleotides mixtures with the sequences SEQ ID NO 3 and SEQ ID NO 4 were designed based on the N-terminal sequence and the internal peptide sequence, respectively.

SEQ ID NO 3: CCA CAR TAY ACI TTC

SEQ ID NO 4: ACN GGY TGY TCR TCC CAA TG

In these sequences, Y stands for T or C, R for A or G, N for A,T,C or G and I for inosine.

The PCR reaction was carried out with 10 ng gDNA of *Penicillium restrictum* A191 in the presence of 10 pmole of the synthetic oligonucleotides mixture with the sequence SEQ ID NO 3. The reaction mix contained also 1 unit rTAQ polymerase (Pharmacia), 200, µM dNTP, 50 mM KCl, 1.5 mM MgCl$_2$ and 10 mM Tris-HCl pH 9.0 in a final volume of 25 µl. After 4 min of denaturation at 94° C., 32 cycles of [30 s 94° C., 30 s 50° C. and 30 s 72° C.] were performed. Between the 4$^{th}$ and 5$^{th}$ cycles, 20 pmoles of the synthetic oligonucleotides mixture with the sequence SEQ ID NO 4 were added to the mixture. A final step of 7 min at 72° C. was applied after the last cycle.

Amplified DNA fragments (c.a. 200 bp) were isolated by agarose gel electrophoresis and purification with the QIAquick gel extraction kit (Qiagen) according to the manufacturer's protocol and recovered in a final volume of 30 µl. Both termini of the isolated fragments were filled using 1 unit Klenow fragment of DNA polymerase I (Pharmacia) in the presence of all four dNTPs (0.5 mM) and 1× One-Phor-All buffer PLUS (Pharmacia). The DNA fragments were again purified with the QiaQuick PCR purification kit (Qiagen) and recovered in a final volume of 30 µl. The DNA fragments were then inserted into a plasmid vector and cloned in *Escherichia coli*. The ligation was performed using 3 µl of DNA fragments, 0.25 µg of EcoRV digested pBluescript SK(+) (Stratagene) plasmid DNA, 3 units of T4 DNA ligase (Pharmacia), 1 mM ATP in a final volume of 30 µl (1× One-Phor-All buffer PLUS, 16° C., 16 h). The ligation mixture was then dialysed on a VSWP 013 membrane (Millipore) against water during 20 min. 1 µl of this ligation mixture was electroporated into 40 µl electrocompetent *Escherichia coli* DH10b cells (BRL-Gibco) according to the BRL-Gibco protocol. After electroporation, cells were plated on LB plates supplemented with 100 µg/ml ampicillin to select the transformed cells.

Plasmid DNA from some transformants were purified using the QIAprep spin miniprep kit (Qiagen). The inserts of the plasmids were sequenced on a ABI 377 sequencer (Applied Biosystem) with 3 pmoles reverse primer. The partial sequence of one of the plasmids was the following:

SEQ ID NO 5:

CACAGTATCACTTNTCTCCTGCTAAG-CACTGGACGAATGATCCCGCTGGTCTCT-TCTATTACGATGGCACCTACCATATGT-TCTTCCAGTACAACCCCGGTGGTATTGAATGGG GCAACATGTCCTGGGGTCATGCTACCAG-CAAAGATCTGACCCATTGGGACGAGCAACCCT

The sequence of SEQ ID NO 5 could be translated into a peptide with the sequence SEQ ID NO 6.

SEQ ID NO 6:

QYHXSPAKHWTNDPAGLFYYDGTYHM-FFQYNPGGIEWGNMS WGHATSKDLTHWDEQP

The sequence of SEQ ID NO 6 shows partial homology with a sucrose:sucrose 1-fructosyltransferase from *Aspergillus foetidus,* a levanase from *Actinomyces naeslundii* and an exo-inulinase from *Pseudomonas mucidolens.*

The 9 last amino acids of the sequence SEQ ID NO 6 are identical to the first 9 amino acids of the sequence SEQ ID NO 2, confirming that the cloned DNA fragment codes to a portion of the inulinase.

Southern Blotting of the *Penicillium restrictum* A191 Genomic DNA

Genomic DNA (0.5 µg) obtained as described above was digested overnight at 37° C. with either 2 units of the restriction enzyme BglI (Pharmacia), or 2 units of each restriction enzymes HindIII and BglI(Pharmacia), or 2 units of each restriction enzymes HindIII in a final volume of 20 µl (buffer: 1× One-Phor-All buffer PLUS (Pharmacia)). The digested DNAs were loaded on a 0.8% agarose gel in 1× TBE buffer. After electrophoresis, the restricted fragments were transferred onto a Hybond-N+ membrane (Amersham). The cloned PCR fragments described above (1 µl) were-labeled with digoxigenin using the DIG High Prime DNA Labeling and Detection Starter Kit II (Boehringer Mannheim). The membrane was hybridized overnight at 42° C. in the presence of a standard hybridization buffer (SSC 5×, formamide 50%, N-lauroylsarcosine 0.1%, SDS 0.02%, Blocking reagent) and a probe concentration of ca. 10 ng/ml (denatured during 5 min at 97° C.). After the hybridization, the membrane was first washed at 55° C. with 2×SSC, 0.1% SDS (2×15 min) followed with 3 washes with a 0.5×SSC, 0.1% SDS solution (30 min). After immunological detection, the hybridizing bands were identified by a 8 hours exposition to a Kodak X-OMAT AR film at room temperature.

The Southern blot revealed that under the hybridization conditions tested, only one DNA fragment hybridized with the probe for each enzyme. The HindIII digestion revealed a DNA fragment of about 5 kb length whereas the HindIII-BglI digestion as well as the BglI alone digestion revealed DNA fragments of the same length (c.a. 1 kb).

Construction and Screening of a gDNA Restriction Fragments Library of *Penicillium restriction* A191

*Penicillium restrictum* A191 genomic DNA (5 µg) was digested overnight at 37° C. with 10 units of restriction enzyme HindIII (Pharmacia) in a final volume of 100 μl. The restriction fragments were separated by electrophoresis on a 0.8% agarose gel in 1× TBE buffer. Pieces of the gel corresponding to DNA fragments between 4.0 and 6.0 kb in length were cut off. The DNA was purified out of these pieces of agarose gel using the Qiaquick gene extraction kit (QIAGEN) and resuspended in a final volume of 50 μl.

The purified fragments were cloned by insertion into the HindIII restriction site of the pBluescript II SK(+) vector (Stratagene). 1 μg of pBluescript SK(+) plasmid DNA was first digested with 5 units of the HindIII restriction enzyme (Pharmacia) in 50 μl (37° C., 16 h) and subsequently purified using the Qiaquick gene extraction kit. The ligation was performed using 3 μl of purified genomic DNA fragments, 0.25 μg of digested pbluescript SK(+) DNA, 3 units of T4 DNA ligase (Pharmacia) and 1 mM ATP in a final volume of 30 μl (1× One-Phor-All buffer PLUS, 16° C., 16 h). The ligation mixture was then dialysed on a VSWP 013 membrane (Millipore) against water during 20 min. 1 μl of this ligation mixture was electroporated into 40 μl electrocompetent *Escherichia coli* DH10b cells (BRL-Gibco) according to the BRL-Gibco protocol. After electroporation, cells were plated on LB plates supplemented with 100 μg/ml ampicillin to select the transformed cells.

The above-described library was screened progressively using PCR reactions on pools of transformants. The PCR reaction conditions were the same as described above with the exception that the template DNA was the mixture of plasmids purified from 3 ml cultures of pooled Escherichia coli transformants with the High Pure Plasmid Isolation Kit (Boehringer Mannheim). A 0.2 kb fragment was amplified in one transformant out of ca. 1200 clones analyzed. The plasmid recovered from this clone (pPRINU) contained a HindIII insert of c.a. 5.5 kb length. An *Escherichia coli* strain containing the plasmid with reference pPRINU has deposited on Oct. 10, 2000 in the Plasmid Collection (BCCM/LMBP) of the Laboratorium Voor Moleculaire Biologic at the Universiteit Gent, Ledenganckstraat, 35, B-9000 Gent, Belgium under the accession number LMBP 4252. A partial sequence of the insert of the pPRINU plasmid was determined on both strands by primer walking using inter alia the oligonucleotides with the sequences SEQ ID NO 7 and SEQ ID NO 8 as sequencing primers.

SEQ ID NO 7: TCT CCT GCT AAG CAC TGG

SEQ ID NO 8: ATG GGT CAG ATC TTT GCT GGT AG

The partial nucleotide sequence (SEQ ID NO 9) obtained for the plasmid pRINU is 2870 bp long and comprises the entire inulinase coding sequence as shown below.

SEQ ID NO 9:
CAGATTCGATCTGGTTAGGCCATATC-
GAACTTCAGTCCGTCACGCACAGTGG-
GACCGCCATTGTACGGCACCATACG-
GCAGGACGAAGTATGCCAATGCACAAACATCG
TGGATAGGTCGGGGATACTTTGCAGCAG-
CATGGCGCCGAGTGATTAGGGAGGTGGT-
TACATCAAACGCAAAAGAGGATCATGGC-
GATACAAAGACATTGGTGAAGCCGGCGGTGGA
GACTGAAAAGGGAAAGCAGGG-
GAAACTCGCGTGGCTGGCAGGGG-
TATAAGCCGAGTATACGCCGTGATGTC-
CGAAATTATCGCTGGGTTTGAGCGATCTCGGTG
CCGAAGCGTGCAGAATCTAGTGCTCAG-
CAGGAAACATTGTGGATCTAAGTT-
TATAATTCTCCGAAGAAACATCGGCGCG-
GATGACGATCGTCCAGCAGGTGGTGACATACC
C CGTGGGGAATGGAGACATTGGGAAAA-
GATATAAATACTGCTTGGAATAATTGT-
GAAGGAATATTTTCATTCAAGCGCT-
TCACTTTCTTTTATTCCTTTTTTTTCTTGCTCCT
TGCATAACTCCACGATGCTCAAGTTTGC-
GAGCGCCTTCGTGTTGGGTCTCCTG-
GCGGGACCCACTGTGGCCGTGAAC-
TATACGGAACCCTTTCGGCCTCAGTATCACTTC
T CTCCTGCTAAGCACTGGACGAATGATC-
CCGCTGGTCTCTTCTATTACGATGGCAC-
CTACCATATGTTCTTCCAGTACAAC-
CCCGGTGGTATTGAATGGGGCAACATGTCCTGG
G GTCATGCTACCAGCAAAGATCTGAC-
CCACTGGGACGAGCAGCCTGTTGCGCT-
TCTCGCAAAGGGTTACCCCAACAACGT-
CACTGAGATGTATTTCACTGGAAGTGCCGTGGC
CGATGTCAACAACACCAGCGGTTTCG-
GCACAGATGGCAAGGTTCCCTTGGTCGC-
TATCTACACCTCTTACGTGAGTATTC-
GACCTAGTTTCTTTTCTTGCGTAGCACTAAATT
GACCATCATTCTTCCTTCATAGTATAC-
CGTCACACAAACCCTGCCCAGCG-
GCAAGCGAGTTCACAAAGACCAG-
CAGTCTCAGTCAATTGCCTACAGTCTGGACAAT
GGCATGACATGGACACCGTACGACTCT-
GTCAACCCTGTGATCCACTACCCTC-
CCCCGCCCTACCACAGCCAGTACAA-
GAACTTCCGTGACCCGTTCGTGTTCTGGCACGA
CCAGACCCAGCGATGGATTCTCGTCAC-
CACCCTGGCTGAACTGCACAAGCTCGT-
GATCTGGACATCCGACAATCTCAAG-
GACTGGACCGTCCTCAGCGAATTCGGCCCCTAC
AATGGCGTCGGGGGTGTGTGGGAGTGC-
CCCAACCTCTTCCCTCTTCCAGTTGACG-
GTGACGGTGACGAGAACATGAC-
CAAGTGGGTCATGGTCGTTGGACTCAACCCCG
GCGGACCACCTGGTACTGTCGGTTCCG-
GAACACAGTACTTTATCGGCAACT-
TCAATGGCACAGCCTTTATTCCGGATGC-
CGATACCATCTACCCCGGAAACAAGACTGCCA
ACTGGATGGACTGGGGCCCGGACTTC-
TACGCTGCTGCCGCTTACAACGGTCTC-
CCTAAGGAGGACCATGTCCAGCTCG-
CATGGATGAATAACTGGCAATATGGTGAACATA
TCCCGACTCACCCCTGGCGAAGCGC-
GATGGCTATCCCTCGTCACCTGTCTCT-
GAAGAACATCGACTCGAAGAC-
GACTCTCGTCCAGCAGCCACACGTGAACTGGA
AATCGATCAAGGGCAAGCATGCTTACAC-
CCGCTTCTGGAAGAGTGTCGACGAAG-
GCATCACAGACCTCGGACCTCTGGGCAA-
GACACTTGCAATCGATATAACCTTTTCCACGCC
CAAGGACGCTGGTTCTCAGAC-
CTTTCAGTTCGGAATCGTCGTCCAGGC-
CACGGAAGACTTGTCCCAACACACGC-
GAGTCGGGTATGATTTCCAGAGTCAGCAGGTCT
TCTTGGACCGCACGCATTCGGGAAT-
TGTCTCATTCGACAAGACCTTCCCGAC-
CGTGTATAACACCACTCTTGCACCGT-
GCTCAGATGGAGAAGTCCGTTTGCAGCTCTTG
GTGGACTGGTCTAGCGTTGAGGTCTTTG-
GTGGTGAGGGCGAGAAGACCGTGACAGC-
CCAGATCTTTCCGAACGAGGAGGCCACA-
CATGTTGAGCTCTTCTCGACTGGTGGAAGCACT
GGGAATGTCAAGGTTGAAATCTGGGAT-
GTGTCCTCGATTTGGAACTGACTGGTG-
CACCGTTAGAAAATAAGAGTATAGAAT-
AGTCCAGGTAGCAAAATAAAGCTATTGGCGAC
ATGTCCATTCAAGATTGGGACCTTC-

CAAACGGTGCATCGAATCAT-
AAAGTCTCTTGAAATCACACATATACAT-
ACGTACATACAAACAGCTCAAACTCAATCACAA
ACAACAAGCGTTCCTCAGAAGCATTGTC-
CGTTCGAATGTCTCCATCAAATCAAT-
GACCCTCGCAGTTACCTCCTTGCACTC-
CTCATTGACATCGCCTTCATCGATAATATCCCCG
AATCGACGCTTCCAGAACCGCCATCTAT-
CAAGGGAAAGACTGGCCTTGCCAT-
GATATAGGGGATCAGGTTCCCAACCCT-
TCCATTCATTGGACGACCCCTGGTAAAGATCCG
GCTATGACGTAAGTTCGAACAAGCTCT-
GACCATACCACAGAATCCATTGGGC-
CGCGCGCGCCTAGGACGAAAGCACTTCG-
CACTTCTTTATCTTTACAGGACAGATCATTCTCC
AAAGCGAAACGCATAGCCCAGATTA-
CATATGTCGGGTCGCATCCGGAAA-
CACGCTGCTCATGGAGGTGGCCACAAAT-
GAGTTATAGTTCA

The nucleotide sequence SEQ ID NO 9 according to the invention contains on the same strand two coding regions for the polypeptides with the amino acid sequences SEQ ID NO 10 and SEQ ID NO 11, and whose lengths are respectively 131 and 412 amino acids.

SEQ ID NO 10:
MLKFASAFVLGLLAGPTVAVNYTEPFR-
PQYHFSPAKHWTNDPAGLFYYDGTYHM-
FFQYNPGGIEWGNMSWGHATSKDLTHWD-
EQPVALLAKGYPNNVTEMYFTGSAVADVNNTSG
FGTDGKVPLVAIYTSY

SEQ ID NO 11:
YTVTQTLPSGKRVHKDQQSQSIAYSLD-
NGMTWTPYDSVNPVIHYPPPPYHSQYKN-
FRDPFVFWHDQTQRWILVTTLAELH-
KLVIWTSDNLKDWTVLSEFGPYNGVGGVWECP
NLFPLPVDGDGDENMTKWVMVVGLNPGG-
PPGTVGSGTQYFIGNFNGTAFIP-
DADTIYPGNKTANWMDWGPDFYAAAAYN-
GLPKEDHVQLAWMNNWQYGEHIPTHPWRSAM
AIPRHLSLKNIDSKTTLVQQPHVNWK-
SIKGKHAYTRFWKSVDEGITDLGPLGKT-
LAIDITFSTPKDAGSQTFQFGIVVQAT-
EDLSQHTRVGYDFQSQQVFLDRTHSGIVSFDKTF
PTVYNTTLAPCSDGEVRLQLLVDWSS-
VEVFGGEGEKTVTAQIFPNEEATHVELF-
STGGSTGNVKVEIWDVSSIWN

Because these two amino acid sequences, SEQ ID NO 10 and SEQ ID NO 11, could be both aligned with the *A. foetidus* sucrose: sucrose 1-fructosyltransferase (emb:CAA04131.1), it is concluded that both sequences are part of the same mature polypeptide and that an intron separates the corresponding nucleotide sequences within the sequence SEQ ID NO 9. The intron presence and localization was also deduced and confirmed from alignments of the *P. restrictum* A191 sequence with other homologous levanase and inulinase protein sequences obtained from a homology search in GENBANK (Oct. 20, 2000) with the BLASTP 2.1.1. software (Altschul et al., 1997, Nucl. Ac. Res., vol 25, p. 3389). This localization was further confirmed by the presence of the putative lariat-formation internal sequence and with the definition of the consensus 5' and 3' splice-junction sequences ('GT-AG' rule).

The sequence SEQ ID NO 12 is the complete amino acid sequence of the *P. restrictum* A191 inulinase according to the invention.

SEQ ID NO 12:
MLKFASAFVLGLLAGPTVAVNYTEPFR-
PQYHFSPAKHWTNDPAGLFYYDGTYHM-
FFQYNPGGIEWGNMSWGHATSKDLTHWD-
EQPVALLAKGYPNNVTEMYFTGSAVADVNNTSG
FGTDGKVPLVAIYTSYYTVTQTLPS-
GKRVHKDQQSQSIAYSLDNGMTWTPYDS-
VNPVIHYPPPPYHSQYKNFRDPFVFWH-
DQTQRWILVTTLAELHKLVIWTSDNLKDWTVLS
EFGPYNGVGGVWECPNLF-
PLPVDGDGDENMTKWVMVVGLNPGGP-
PGTVGSGTQYFIGNFNGTAFIP-
DADTIYPGNKTANWMDWGPDFYAAAAYNGLPK
EDHVQLAWMNNWQYGEHIPTHPWRSA-
MAIPRHLSLKNIDSKTTLVQQPHVNWK-
SIKGKHAYTRFWKSVDEGITDLGPLGKT-
LAIDITFSTPKDAGSQTFQFGIVVQATEDLSQHTR
VGYDFQSQQVFLDRTHSGIVSFDKTF-
PTVYNTTLAPCSDGEVRLQLLVDWSS-
VEVFGGEGEKTVTAQIFPNEEATHVELF-
STGGSTGNVKVEIWDVSSIWN

Figures 5, 5A, 5B, 5C, 5D, 5E:
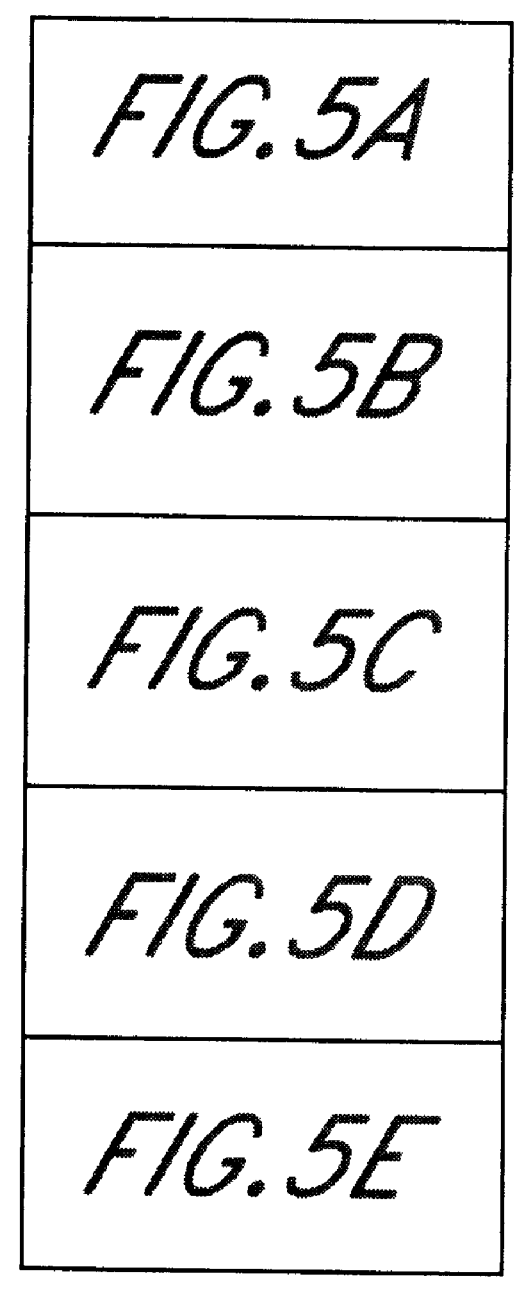

A signal sequence driving the secretion of the enzyme covers the 19 first amino acids of the sequence. The amino acid sequence SEQ ID NO 13 represent the sequence of the mature protein. The mature inulinase is 524 amino acids long. The calculated molecular weight is 58.860 Da. This indicates that the inulinase secreted by *Penicillium restrictum* A191 is modified post-translationally e.g. by glycosylation. The FIG. 5 shows the complete sequence of the inulinase gene as well as the corresponding amino-acid sequence, the position of the intron and the position of the signal sequence.

SEQ ID NO 13:
VNYTEPFRPQYHFSPAKHWTNDPA-
GLFYYDGTYHMFFQYNPGGIEWGNM-
SWGHATSKDLTHWDEQPVALLAKGYPN-
NVTEMYFTGSAVADVNNTSGFGTDGKVPLVAIYT
SYYTVTQTLPSGKRVHKDQQSQSIAY-
SLDNGMTWTPYDSVNPVIHYPPPPYH-
SQYKNFRDPFVFWHDQTQRWILVT-
TLAELHKLVIWTSDNLKDWTVLSEFGPYNGVGG
VWECPNLFPLPVDGDGDENMTKWVMV-
VGLNPGGPPGTVGSGTQYFIGNFNG-
TAFIPDADTIYPGNKTANWMDWGPD-
FYAAAAYNGLPKEDHVQLAWMNNWQYGEHIPT
HPWRSAMAIPRHLSLKNIDSKT-
TLVQQPHVNWKSIKGKHAYTRFWKSVDE-
GITDLGPLGKTLAIDITFSTPKDAGSQT-
FQFGIVVQATEDLSQHTRVGYDFQSQQVFLDRTH
SGIVSFDKTFPTVYNTTLAPCSDGEVR-
LQLLVDWSSVEVFGGEGEKTVTAQIFP-
NEEATHVELFSTGGSTGNVKVEIWDVSSIWN

The inverse complementary nucleotide sequence of the sequence SEQ ID NO 9 contains another 918 bp length open reading frame (ORF). This ORF is located into the region encoding the inulinase protein, but on the other strand in the opposite direction. The ORF encodes a putative amino acid sequence of 306 amino acids (SEQ ID NO 14) with no known homologous protein as deduced from a homology search in GENBANK (Oct. 20, 2000) with the BLASTP 2.1.1. software.

SEQ ID NO 14:
MRAVQEDLLTLEIIPDSRVLGQVFRGLD-
DDSELKGLRTSVLGRGKGYIDCK-
CLAQRSEVCDAFVDTLPEAGVSMLA-
LDRFPVHVWLLDESRLRVDVLQRQVTRDSHRAS
PGVSRDMFTILPVIHPCELDMVLLRETV-
VSGSSVEVRAPVHPVGSLVSGVDGI-

GIRNKGCAIEVADKVLCSGTDSTR-
WSAGVESNDHDPLGHVLVTVTVNWKREEVGAL
PHTPDAIVGAEFAEDGPVLEIVGCPD-
HELVQFSQGGDENPSLGLVVPE-
HERVTEVLVLAVVGRGRVVDHRVDRV-
VRCPCHAIVQTVGN

Example 7

Expression of the Inulinolytic Enzyme Gene in *Aspergillus orzyae*

Construction of Expression Vectors

A DNA fragment covering the *Penicillium restrictum* A191 inulinase coding region as well as its terminator region was amplified by PCR. The first synthetic oligonucleotide used as primer (SEQ ID NO 15) was chosen to contain the ATG codon corresponding to the first methionine of the coding region of the polypeptide as well as a recognition site for the restriction enzyme NcoI. The second primer oligonucleotide was the M13/pUC Reverse Sequencing Primer (cat No#S1201S New England Biolabs Inc.).

SEQ ID NO 15: TCCACCATGGTCAAGTTTGC-
GAGCGCCTTCG

Both primers (40 pmoles) were used for a PCR reaction with ca. 40 ng of pPRINU plasmid DNA as template. The 100 μl PCR reaction contained also 2.5 units Pfu DNA polymerase (Stratagene) and 1 μg BSA in the following buffer: Tris-HCl pH 8.0 20 mM, KCl 10 mM, $MgCl_2$ 2 mM, $(NH_4)_2SO_4$ 6 mM and Triton X-100 0.1%. After denaturation of the DNA during 4 min at 94° C., 15 cycles of elongation were performed [30s at 94° C., 30 s at 55° C. and 180 s at 72° C.] followed by a final elongation step of 7 min at 72° C. The amplified DNA fragment was purified with the QiaQuick PCR purification kit (Qiagen) according to the manufacturer's protocol and recovered in a final volume of 50 μl. The extremities of the fragment were removed by digestion with the NcoI and HindIII restriction enzymes (5 units of each enzyme (Pharmacia), 1× One-Phor-All buffer PLUS, final volume 60 μl, 37° C., overnight). The fragment was then purified with the QIAquick gel extraction kit (Qiagen) after separation by electrophoresis on an agarose gel in 1×TBE buffer and recovered in 30 μl water.

The inulinase encoding gene was ligated downstream of the glyceraldehyde-3-P dehydrogenase promotor of *A. nidulans*. This promoter allows a strong constitutive transcription of the genes located downstream of it (Punt et al., 1990, Gene, vol 93, p. 101; Punt et al., 1991, J. Biotechnol., vol 17, p. 19). The plasmid pFGPDGLAT2 contains this promoter followed by two restriction sites NcoI and HindIII between which protein encoding nucleotide sequences can be inserted.

The vector was prepared as follows: 0.5 μg pFGPDG-LAT2 DNA was digested with 5 units each of the NcoI and HindIII restriction enzymes (Pharmacia) (final volume 20 μl, 2× One-Phor-All buffer PLUS, 37° C., overnight). After separation by agarose gel electrophoresis, the open vector was purified with the QIAquick gel extraction kit (Qiagen) and recovered in 30 μl water.

2 μl of the PCR DNA fragment were ligated with this vector (1 μl) in the presence of ATP (1 mM), 1 unit of T4 DNA ligase (Pharmacia) and 1× One-Phor-All buffer PLUS (final volume 10 μl, 16° C., overnight). 1 μl of the ligation mixture was electroporated into competent *Escherichia coli* JM109 cells after dialysis against water. A positive clone was selected after analysis of some transformants by plasmid extraction, plasmid digestion with the appropriate restriction enzymes and separation of the DNA fragments by agarose gel electrophoresis using standard procedures. The new plasmid was termed pGPD-PRINU.

Transformation of *Aspergillus oryzae*

The strain *Aspergillus oryzae* MUCL 14492 was transformed by generating protoplasts according to the protocol described by Punt et al. (Meth. Enzymol, 1992, vol 216, p. 447). The pGPD-PRINU plasmid was cotransformed with the p3SR2 plasmid that contains a selection marker used to recover transformants (the *Aspergillus nidulans* acetamidase gene—Hynes et al., 1983, Mol. Cell. Biol., vol 3, p. 1430). Transformants were selected on minimum medium plates containing acetamide as sole nitrogen source.

The strain *Aspergillus oryzae* MUCL 14492 was grown in 500 ml Aspergillus Minimum Liquid medium (Pontecorvo et al., 1953, op. cit.) during 16 hours at 30° C. The culture was filtered through a Miracloth filter to collect the mycelium. The mycelium was washed with the Osm solution ($CaCl_2$ 0.27 M, NaCl 0.6 M). and then incubated with 20 ml solution Osm/g mycelium supplemented with 20 mg Novozym 234 (Sigma). After 1 hour at 30° C. with slow agitation (80 rpm), the protoplasts were formed and the suspension was putted on ice. The protoplasts were separated from intact mycelium by filtration through a sterile Miracloth filter and diluted with 1 volume STC1700 solution (sorbitol 1.2 M, Tris-HCl pH 7.5 10 mM, $CaCl_2$ 50 mM, NaCl 35 mM). The protoplasts were then collected by centrifugation at 2000 rpm, 10 min, 4° C. and washed twice with STC1700 solution. They were resuspended in 100 μl of STC1700 (108 protoplasts/ml) in the presence of 3 μg p3SR2 plasmid DNA and 9 μg pGPD-PRINU plasmid DNA. After 20 min at 20° C., 250, 250 and 850 μl PEG solution (PEG 4000 60%, Tris-HCl pH 7.5 10 mM and $CaCl_2$ 50 mM) were added successively and the suspension was further incubated for 20 min at 20° C. PEG treated protoplast suspensions were diluted by the addition of 10 ml STC1700 and centrifuged 10 min at 4° C., 2000 rpm. The protoplasts were then resuspended in 200 μl STC 1700 and plated onto Aspergillus Minimum Agar Medium osmotically stabilized with 1.2 M sorbitol. To select the transformants, the nitrogen sources in the plates were replaced by 10 mM acetamide and 12 mM CsCl.

Analysis of *Aspergillus oryzae* Transformants 22 transformants were analyzed for their inulolytic enzyme expression. They were grown in Aspergillus Minimum Liquid Medium supplemented with 3% sucrose as carbon source and 0.5% Bacto yeast extract (Difco). After 75 hours at 30° C. and 130 rpm, the supernatants of the cultures were assayed for inulinase activity. 5 transformants showed a significantly higher inulolytic activity as compared to a control strain transformed only with the p3SR2 plasmid.

What is claimed is:

1. An isolated and purified polypeptide with inulinolytic activity having greater than 75% sequence identity with SEQ ID NO: 12.

2. The polypeptide of claim 1, having greater than 80% sequence identity with SEQ ID NO 12.

3. An isolated and purified polypeptide sequence comprising SEQ ID NO 12 or a portion thereof having inulinolytic activity.

4. The polypeptide of claim 1, wherein said polypeptide has an optimum enzymatic activity at a pH between about 4.0 and about 6.0 and at a temperature between about 60° C. and about 70° C.

* * * * *